(12) United States Patent
Lee et al.

(10) Patent No.: US 9,315,507 B2
(45) Date of Patent: Apr. 19, 2016

(54) COMPOUNDS AS HIF-1ALPHA INHIBITORS AND MANUFACTURING PROCESS THEREOF

(71) Applicants: DONGGUK UNIVERSITY INDUSTRY-ACADEMIC COOPERATION FOUNDATION, Seoul (KR); KOREA RESEARCH INSTITUTE OF BIOSCIENCE AND BIOTECHNOLOGY, Daejeon (KR)

(72) Inventors: Kyeong Lee, Seoul (KR); Mi-Sun Won, Daejeon (KR); Hwan-Mook Kim, Daejeon (KR); Song-Kyu Park, Daejeon (KR); Ki-Ho Lee, Seoul (KR); Chang-Woo Lee, Chungcheongbuk-do (KR); Bo-Kyung Kim, Seoul (KR); Hyun-Seung Ban, Daejeon (KR); Kyung-Sook Chung, Daejeon (KR); Naik Ravi, Seoul (KR)

(73) Assignees: Dongguk University Industry-Academic Cooperation Foundation, Seoul (KR); Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/347,556

(22) PCT Filed: Sep. 27, 2012

(86) PCT No.: PCT/KR2012/007876
§ 371 (c)(1),
(2) Date: Mar. 26, 2014

(87) PCT Pub. No.: WO2013/048164
PCT Pub. Date: Apr. 4, 2013

(65) Prior Publication Data
US 2014/0228357 A1    Aug. 14, 2014

(30) Foreign Application Priority Data

Sep. 27, 2011   (KR) .................. 10-2011-0097355
Sep. 26, 2012   (KR) .................. 10-2012-0107494

(51) Int. Cl.
| | | |
|---|---|---|
| C07D 487/04 | (2006.01) |
| C07D 295/185 | (2006.01) |
| C07C 235/20 | (2006.01) |
| C07C 235/22 | (2006.01) |
| C07D 295/073 | (2006.01) |
| C07D 241/04 | (2006.01) |
| C07C 231/02 | (2006.01) |
| C07D 295/108 | (2006.01) |
| C07D 295/182 | (2006.01) |
| C07D 307/52 | (2006.01) |

(52) U.S. Cl.
CPC .......... *C07D 487/04* (2013.01); *C07C 231/02* (2013.01); *C07C 235/20* (2013.01); *C07C 235/22* (2013.01); *C07D 241/04* (2013.01); *C07D 295/073* (2013.01); *C07D 295/108* (2013.01); *C07D 295/182* (2013.01); *C07D 295/185* (2013.01)

(58) Field of Classification Search
None
See application file for complete search history.

(56) References Cited

U.S. PATENT DOCUMENTS 6,207,665 B1 *  3/2001  Bauman et al. ............ 514/235.8

FOREIGN PATENT DOCUMENTS

| JP | 2002503239 A | 1/2002 |
| WO | WO 2008-004798 A1 | 1/2008 |
| WO | WO 2010/056048 A2 | 5/2010 |
| WO | WO 2011/014009 A2 | 3/2011 |

OTHER PUBLICATIONS

CA Registry No. 611196-32-8, entered into the Registry File on Oct. 31, 2003, supplied by Ambinter.*
About Ambinter, 2 page retrieved from the Internet at http://www.ambinter.com/about-us on Mar. 17, 2015.*
K. Lee, et al; (Aryloxyacetylamino)benzoic acid analogues; a new class of . . . ; J. Med. Chem., vol. 50; 2007; pp. 1675-1684.
S.K. Boovanahalli, et al; Synthesis of (aryloxyacetylamino)-isonicotinic/nicotine acid . . . ; Bioorganic & Medicinal Chem. Letters; vol. 17; 2007; pp. 6305-6310.
J.Y. Chung, et al; Pharmacophore-based 3D QSAR of HIF-1 inhibitors; Arch. Pharm. Res.; vol. 32(3); 2009; pp. 317-323.
C. Blancher et al; The molecular basis of the hypoxia response pathway: Tumour . . . ; Cancer and Metastasis Reviews; vol. 17; 1998; pp. 187-194.
G.L. Semenza; Hypoxia-inducible factor 1; oxygen homeostasis and disease pathophysiology; Trends Mol. Med.; vol. 7; No. 8; 2001; p. 345-350.
P. Jaakkola et al; Targeting of HIF-a to the von Hippel-Lindau . . . ; Science; vol. 292; 2001; pp. 468-472.

(Continued)

*Primary Examiner* — Emily Bernhardt
(74) *Attorney, Agent, or Firm* — Lucas & Mercanti, LLP

(57) ABSTRACT

The present invention relates to novel compounds as HIF-1α inhibitors, manufacturing process thereof, and a pharmaceutical compositions. The compounds according to the present invention having inhibition activity against HIF-1α, can be used as a therapeutic prevention and/or treatment for various solid cancers such as colon cancer, liver cancer, stomach cancer and breast cancer. Also, the compounds according to the present invention are useful in the treatment of diabetic retinopathy and rheumatoid arthritis, which are aggravated by HIF-1α-mediated VEGFA expression.

3 Claims, 1 Drawing Sheet

(56) References Cited

OTHER PUBLICATIONS

A.L. Harris; Hypoxia—a key regulatory factor in tumour growth; Nat. Rev. Cancer; vol. 2; 2002; pp. 38-47.

L.E. Huang et al; Hypoxia-inducible factor and its biomedical relevance; J. Biol. Chem.; vol. 278; 2003; pp. 19575-19578.

C.W. Pugh et al; Regulation of angiogenesis by hypoxia; role of the . . . ; Nat. Med.; vol. 9; No. 6; 2003; pp. 677-684.

G.L. Semenza; Signal transduction to hypoxia-inducible factor 1; Biochem. Pharmacol.; vol. 64; 2002; pp. 993-998.

E. Maltepe, et al; Abnormal angiogenesis and responses to glucose and . . . ; Nature; vol. 386; 1997; pp. 403-407.

Ch. Kouroussis, et al; Oxaliplatin in combination with infusional . . . ; Oncol.; vol. 28; 2001; pp. 36-41.

A.L. Kung, et al; Suppression of tumor growth through disruption of . . . ; Nat. Med.; vol. 6; No. 12; 2000; pp. 1335-1340.

R. Bos, et al; Levels of hypoxia-inducible factor-1 . . . ; Am. Can. Society; vol. 97; 2003; pp. 1573-1581.

A. Rapisarda, et al; Identification of small molecule inhibitors of . . . ; Cancer Research; vol. 62; 2002; pp. 4316-4324.

Nat. Rev. Drug Discov. vol. 2; 2003; pp. 1-9.

G.L. Semenza; Targeting HIF-1 for cancer therapy; Nat. Rev. Cancer; vol. 3; 2003; pp. 721-732.

E. Yeo, et al; YC-1: A potential anticancer drug targeting hypoxia-inducible factor 1; Journ. Nat. Can. Inst.; vol. 95; No. 7; 2003; pp. 516-525.

N. Chau, et al; Identification of novel small molecule inhibitors . . . ; Cancer Res.; vol. 65; 2005: pp. 4918-4928.

A.L. Kung, et al; Small molecule blockade of transcriptional coactivation . . . ; Cancer Cell; vol. 6; 2004; pp. 33-43.

E. Ikeda; Cellular response to tissue hypoxia and its involvement in . . . ; Pathol. Int.; vol. 55; 2005; pp. 603-610.

International Search Report dated Mar. 12, 2013 for PCT/KR2012/007876.

David R. Goode, et al. "Identification of Promiscuous Small Molecule Activators in High-Throughput Enzyme Activation Screens" J. Med. Chem. 2008, vol. 51, No. 8, 2346-2349.

Australian Paent Examination Report No. 1. for Australiann Patent Application No. 2012316941, (2015).

European Search Report for Application No./Patent No. 12837558.1, (2015).

Registry Copyright 2015 ACS on STN; Database: ChemBridge Corporation; RN 1052414-33-1 Registry, (2008).

* cited by examiner

COMPOUNDS AS HIF-1ALPHA INHIBITORS AND MANUFACTURING PROCESS THEREOF

CROSS-REFERENCE TO RELATED APPLICATIONS

This application is a 371 of PCT/KR2012/007876, filed Sep. 27, 2012, which claims the benefit of Korean Patent Application No. 10-2011-0097355, filed Sep. 27, 2011 and of Korean Patent Application No. 10-2012-0107494, filed Sep. 26, 2012, the contents of each of which are incorporated herein by reference.

TECHNICAL FIELD

The present invention relates to novel compounds as HIF-1α inhibitors, manufacturing process thereof, and a pharmaceutical use comprising the same as an effective component.

BACKGROUND ART

In spite of extensive efforts conducted for decades all over the world, cancer still remains one of the most incurable diseases. Recently, with great and brilliant advances in all sorts of sciences comprising cancer biology and medicinal chemistry, anticancer agents such as Gleevec, which have innovative mechanisms, have been developed. Since the completion of the Human Genome Project, new molecules that are targets of anticancer agents have been discovered.

HIF-1 (Hypoxia Inducible Factor-1) is a heterodimeric transcription factor composed of two subunits: HIF-1α subunit, an oxygen-dependent decomposition domain; and HIF-1β subunit, a constitutively expressed domain [Cancer Metastasis Rev. 17, 187-195, 1998; Trends Mol. Med. 7, 345-350, 2001]. Under normal oxygen concentrations, the HIF-1α protein is hydroxylated depending on the oxygen at proline residues 402 and 564, thereby it will be ubiquitinated by interacting the tumor suppressor pVHL (von Hippel-Lindau) and decomposed by proteasome. In hypoxia, however, these consecutive reactions are inhibited, so that the HIF-1α protein is α-cumulated and translocated as a dimeric complex associated with the preexisting HIF-1β protein into the nucleus [Science 292, 468-472, 2001]. HIF-1β expression is relatively constant, therefore HIF-1 action depends on the stability and expression regulation of HIF-1α mainly. The stability of HIF-1α depends not only on partial oxygen pressure but also on factors involved in an oxygen sensing pathway, including transition metal ions, iron chelators, and antioxidants. In addition, the HIF-1α protein can accumulate irrespective of oxygen concentrations by activation of growth factors, such as epidermal growth factor, heregulin, insulin-like growth factor-I, insulin-like growth factor-II, etc., or of oncogenes, such as Her2 oncogene (Human Epidermal Growth Factor Receptor 2), etc. When these growth factors bind to respective receptors, HIF-1α protein is synthesized by activating the PI3K-AKT or MAPK signal transduction pathway, with the result that the HIF-1α protein accumulates.

Within a nucleus, HIF-1α/HIF-1β is associated with an HRE (Hypoxia Responsive Element, 5'-ACGTG-3') on the promoter of a target gene to induce the expression of the gene. There are about 60 genes that have been known to be regulated by HIF-1, including a vascular endothelial growth factor (VEGF) gene [Nat. Rev. Cancer 2, 38-47, 2002; J. Biol. Chem. 278, 19575-19578, 2003; Nat, Med. 9, 677-684, 2003; Biochem. Pharmacol. 64, 993-998, 2002].

Hypoxia is usual in cancer, in particular solid cancer. Because solid cancer cells are adapted to a low oxygen condition after being subjected to various genetic alterations, they become more malignant and resistant to anticancer agents. In fact, hypoxia is known to play an important role in malignant cancer in over 70% of all cancer types [Nature 386, 403, 1997; Oncol. 28, 36-41, 2001, Nat. Med. 6, 1335, 2000; Cancer 97, 1573-1581, 2003].

HIF-1 is one of the most important molecules regulating the adaptation of cancer cells to hypoxia, and the amount of HIF-1α protein is closely correlated with poor prognosis of cancer patients. Whether attributed to the hypoxia, or above-mentioned the stimulation of growth factors or the activation of oncogenes, or the inactivation of tumor suppressors, such as pVHL, the cancer cells are activated, HIF-1α induces the expression of various genes encoding, for example, hexokinase 2, glucose transporter 1, erythropoietin, IGF-2, endoglin, VEGF, MMP-2, uPAR, MDR1, etc., leading to improvement in apoptosis resistance, angiogenesis, cell proliferation, and invasiveness, thereby resulting in the malignant transformation of cancer cells.

In addition, it is known that HIF-1 overexpression increased patient mortality through tumor growth stimulation and resistance to chemotherapy and radiation. Because it plays a pivotal role in the growth, proliferation and malignant transformation of cancer, in particular, solid cancer, HIF-1 has become a major target of many anticancer agents, and active and extensive research has been conducted thereon [Cancer Res. 62, 4316, 2002; Nat. Rev. Drug Discov. 2, 1, 2003; Nat. Rev. Cancer 3, 721-732, 2003].

Recently, a significant number of preexisting anticancer agents, such as taxol, rafamycin and 17-AAG (17-allylaminogeldanamycin), or small molecular compound YC-1 (3-(5'-hydroxymethyl-2'-furyl)-1-benzylindazole) are undergoing various clinical demonstrations for use as HIF-1α inhibitors [Nat. Rev. Drug Discov. 2, I-9, 2003; Nat. Rev. Cancer 3, 721-732, 2003; JNCI-95, 516, 2003], and cell based reporter assays for screening HIF-1α inhibitors of new structures are being actively conducted by taking advantage of HRE [Cancer Res. 65, 4918, 2005; Cancer Cell 6, 33, 2004; Cancer Res. 62, 4316, 2002]. However, these are in the early stage of drug discovery.

HIF-1α can be used as a valid target for novel anticancer therapeutics. Angiogenesis factors which are derived by an activated HIF-1α in hypoxia condition, such as VEGF, are associated with the progress of diabetic retinopathy and rheumatoid arthritis as well as cancer.

In addition, the compounds that inhibit an activated HIF-1α from hypoxia condition can also be used as novel therapeutics for the diseases comprising diabetic retinopathy and rheumatoid arthritis [Pathol. Int. 55, 603-610, 2005].

Consequently, the present inventors have prepared compounds that inhibit the HIF-1α activity and angiogenesis excellently, and have high safety in vivo. Therefore, HIF-1α inhibitors, treating the disease comprising diabetic retinopathy and rheumatoid arthritis which are derived by an activated HIF-1α, are developed.

DISCLOSURE OF INVENTION

Technical Problem

Accordingly, the present invention is designed to provide novel compound having inhibition activity against the transcription factor HIF-1α and manufacturing process thereof.

It is another object of the present invention is to provide pharmaceutical uses of HIF-1α inhibitors that can be useful for treating cancer, diabetic retinopathy, and rheumatoid arthritis by showing HIF-1α inhibitory activity.

However, the technical objects to be achieved in the present invention are not limited to those stated above and other objects may be clearly understood to those skilled in the art from the following description.

Solution to Problem

To solve the problem described above, the present invention provides novel compounds of Formula I, pharmaceutically acceptable salts, hydrates or solvates thereof.

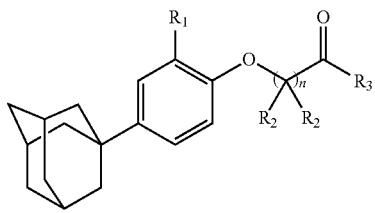

<Formula I> wherein,
R₁ represents hydrogen, methyl, fluoro or chloro;
R₂ represents hydrogen or methyl;
R₃ represents,

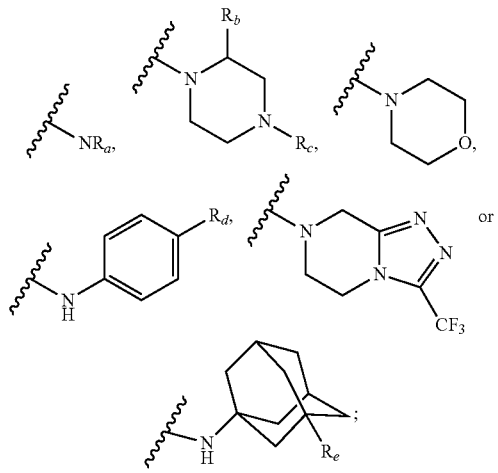

n represents 1, 2 or 3;
especially,
R$_a$ represents dimethyl, cyclopropyl, N,N-dimethylaminoethyl or 2-furanylmethyl;
R$_b$ represents hydrogen, (S)-methyl or (R)-methyl;
R$_c$ represents hydrogen, methyl, isopropyl, tert-butoxycarbonyl(Boc), 4-trifluoromethylbenzyl, hydroxyethyl or propynyl;
R$_d$ represents

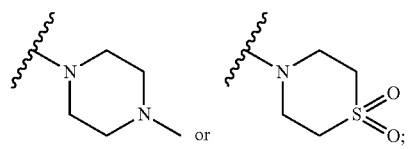

R$_e$ represents hydrogen or hydroxyl.

Preferred examples of the compound of Formula I according to the present invention comprise the followings:
2-(4-(Adamantan-1-yl)phenoxy)-N,N-dimethylacetamide (I-1);
2-(4-(Adamantan-1-yl)phenoxy)-N-cyclopropylacetamide (I-2);
2-(4-(Adamantan-1-yl)phenoxy)-1-(4-methylpiperazin-1-yl)ethanone (I-3);
2-(4-(Adamantan-1-yl)-2-methylphenoxy)-1-(4-methylpiperazin-1-yl)ethanone (I-5);
2-(4-(Adamantan-1-yl)-2-methylphenoxy)-1-morpholinoethanone (I-6);
2-(4-(Adamantan-1-yl)-2-methylphenoxy)-N-(2-(dimethylamino)ethyl)acetamide (I-7),
3-(4-(Adamantan-1-yl)phenoxy)-1-(4-methylpiperazin-1-yl)propan-1-one (I-8);
3-(4-(Adamantan-1-yl)phenoxy)-1-morpholinopropan-1-one (I-9);
3-(4-(Adamantan-1-yl)phenoxy)-N-(2-(dimethylamino)ethyl)propanamide (I-10);
3-(4-(Adamantan-1-yl)-2-methylphenoxy)-1-(4-methylpiperazin-1-yl)propan-1-one (I-11);
3-(4-(Adamantan-1-yl)-2-methylphenoxy)-1-morpholinopropan-1-one (I-12);
3-(4-(Adamantan-1-yl)-2-methylphenoxy)-N-(2-(dimethylamino)ethyl)propanamide (I-13);
4-(4-(Adamantan-1-yl)phenoxy)-1-(4-methylpiperazin-1-yl)butan-1-one (I-14);
2-(4-(Adamantan-1-yl)phenoxy)-2-methyl-1-(4-methylpiperazin-1-yl)propan-1-one (I-23);
2-(4-(Adamantan-1-yl)phenoxy)-N-(2-(dimethylamino)ethyl)-2-methylpropanamide (I-24);
2-(4-(Adamantan-1-yl)-2-fluorophenoxy)-1-(4-methylpiperazin-1-yl)ethanone (I-25);
2-(4-(Adamantan-1-yl)phenoxy)-N-(furan-2-ylmethyl)acetamide (I-26);
2-(4-(Adamantan-1-yl)phenoxy)-1-(4-(4-(trifluoromethyl)benzyl)piperazin-1-yl)ethanone (I-27);
2-(4-(Adamantan-1-yl)phenoxy)-1-(4-isopropylpiperazin-1-yl)ethanone (I-28);
tert-Butyl 4-(2-(4-(Adamantan-1-yl)phenoxy)acetyl)piperazine-1-carboxylate (I-29);
2-(4-(Adamantan-1-yl)phenoxy)-1-(piperazin-1-yl)ethanone (I-30);
(S)-tert-Butyl 4-(2-(4-(adamantan-1-yl)phenoxy)acetyl)-3-methylpiperazine-1-carboxylate (I-31);
2-(4-(Adamantan-1-yl)phenoxy)-1-((S)-2-methylpiperazin-1-yl)ethanone (I-32);
(R)-tert-Butyl 4-(2-(4-(adamantan-1-yl)phenoxy)acetyl)-3-methylpiperazin-1-carboxylate (I-33);
2-(4-(Adamantan-1-yl)phenoxy)-1-((R)-2-methylpiperazin-1-yl)ethanone (I-34);
2-(4-(Adamantan-1-yl)phenoxy)-1-(4-(2-hydroxyethyl)piperazin-1-yl)ethanone (I-35);
2-(4-(Adamantan-1-yl)phenoxy)-1-(4-(prop-2-yn-1-yl)piperazin-1-yl)ethanone (I-36);
2-(4-(Adamantan-1-yl)phenoxy)-N-(4-(4-methylpiperazin-1-yl)phenyl)acetamide (I-37);
2-(4-(Adamantan-1-yl)phenoxy)-N-(4-(1,1-dioxidothiomorpholino)phenyl)acetamide (I-38);
2-(4-(Adamantan-1-yl)phenoxy)-1-(3-(trifluoromethyl)-5,6-dihydro-[1,2,4]triazolo[4,3-a]pyrazin-7(8H)-yl)ethanone (I-39);

N-(Adamantan-1-yl)-2-(4-adamantan-1-yl)phenoxy)acetamide (I-40);
2-(4-(Adamantan-1-yl)phenoxy)-N-(3-hydroxyadamantan-1-yl)acetamide (I-41); and
2-(4-(Adamantan-1-yl)-2-chlorophenoxy)-1-(4-methylpiperazin-1-yl)ethanone (I-42).

The compounds according to the present invention can contain one or more actual or potential chiral centres because of the presence of asymmetric carbon atoms. The presence of asymmetric carbon atoms can give rise to a number of diastereoisomers with R or S stereochemistry at each chiral centre. Therefore, the compounds according to the present invention include all such diastereoisomers and mixtures thereof.

The compound of Formula I according to the present invention can be prepared using various methods, and an example of the present invention can be prepared in Scheme 1.

<Scheme 1>

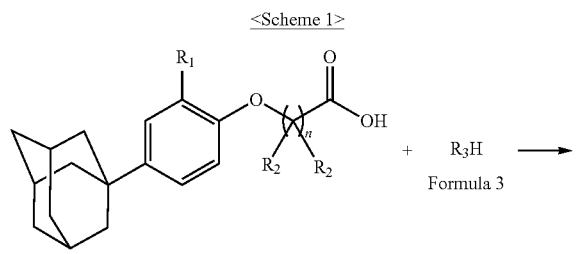

Formula 2

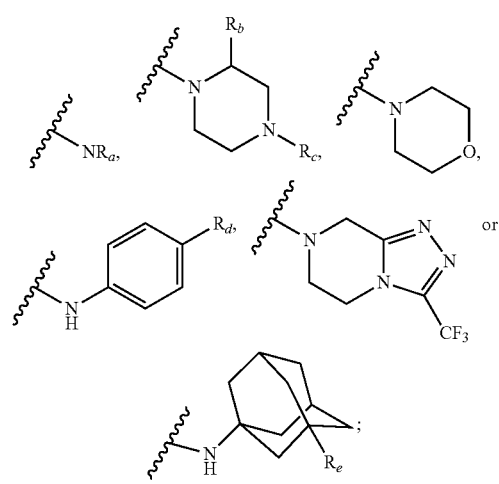

Formula 1

$R_1$, $R_2$, $R_3$ and n illustrated in Scheme 1, are the same as defined in Formula I.
wherein,
$R_1$ represents hydrogen, methyl, fluoro or chloro;
$R_2$ represents hydrogen or methyl;
$R_3$ represents,

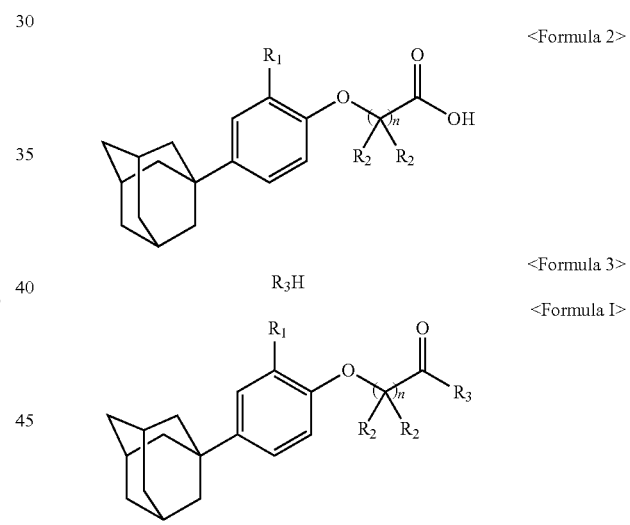

especially, $R_a$ represents dimethyl, cyclopropyl, N,N-dimethylaminoethyl or 2-furanylmethyl;

$R_b$ represents hydrogen, (S)-methyl or (R)-methyl;

$R_c$ represents methyl, isopropyl, tert-butoxycarbonyl (Boc), 4-trifluoromethylbenzyl, hydroxyethyl or propynyl;

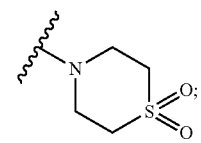 [SMILES: *N1CCS(=O)(=O)CC1]

$R_e$ represents hydrogen or hydroxyl;
n represents 1, 2 or 3.

In detail, the preparation method of the compounds of Formula I according to the present invention can be prepared a compound of Formula I form a compound of Formula 2 as a start substance which reacts with Formula 3, 1-ethyl-3-(3-dimethylaminopropyl)carbodiimide (EDCI), 1-Hydroxybenzotriazole hydrate (HOBt) and N,N-diisopropylethylamine (DIPEA) by coupling reaction in dimethylformamide (DMF).

$R_1$, $R_2$, $R_3$ and n are the same as defined in Formula I.

In addition, the compound of Formula 2 used as a start substance in the present invention can be prepared using Scheme 2.

An example in the present invention, the process for preparing above compounds of formula 2 is followed by below steps:

Preparing a compound of Formula 6 from Formula 4 which reacts with Formula 5 by substitution (Step 1);

Preparing a compound of Formula 7 from Formula 6 by demethylation (Step 2);

Preparing a compound of Formula 9 from Formula 7 which reacts with Formula 8 by alkylation (Step 3); and Preparing a compound of Formula 2 from Formula 9 by hydrolysis (Step 4).

<Scheme 2>

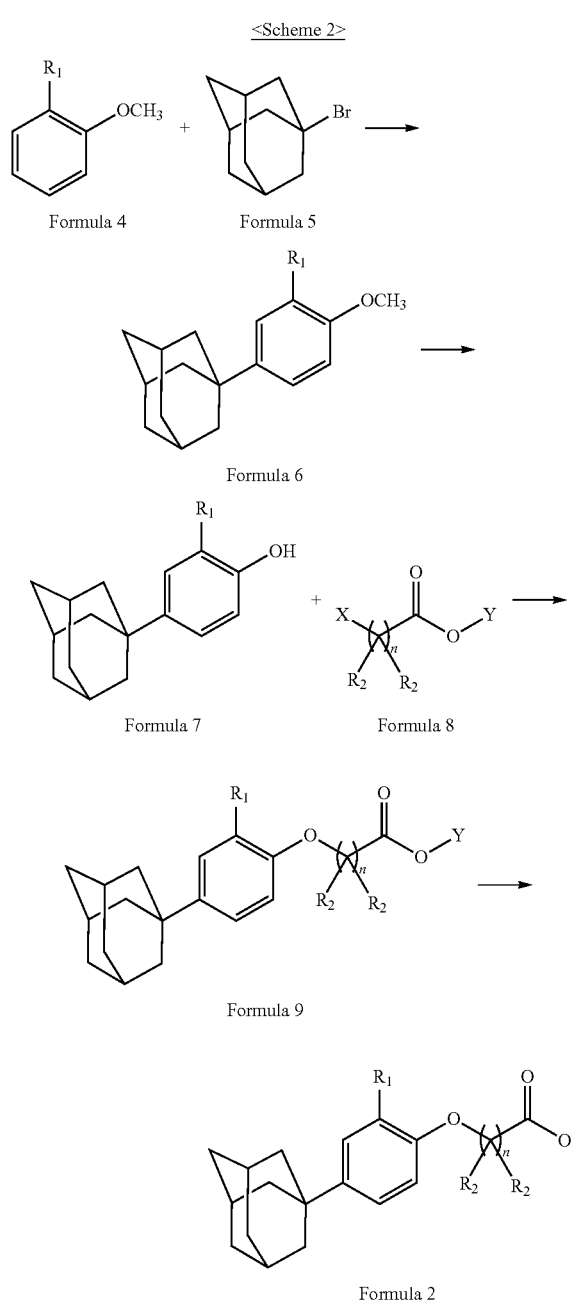

Each step of the above preparation method is described in more detail as below.

i) The compound of Formula 6 can be prepared from the compound of Formula 4 by substitution reaction with the compound of Formula 5, potassium carbonate and 10% palladium/charcoal (Pd/C). An example of the above reaction is illustrated below.

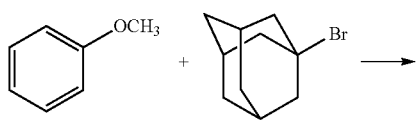

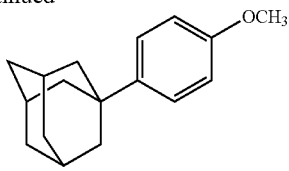

ii) The compound of Formula 7 can be prepared from the compound of Formula 6 by demethylation reaction with boron tribromide ($BBr_3$). An example of the above reaction is illustrated below.

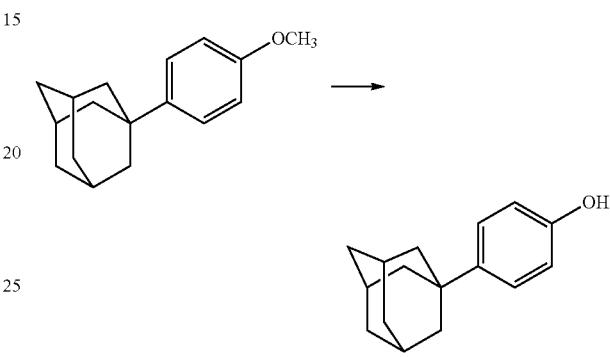

iii) The compound of Formula 9 can be prepared from the compound of Formula 7 by alkylation reaction with the compound of Formula 8 and anhydrous potassium carbonate in DMF at room temperature. An example of the above reaction is illustrated below.

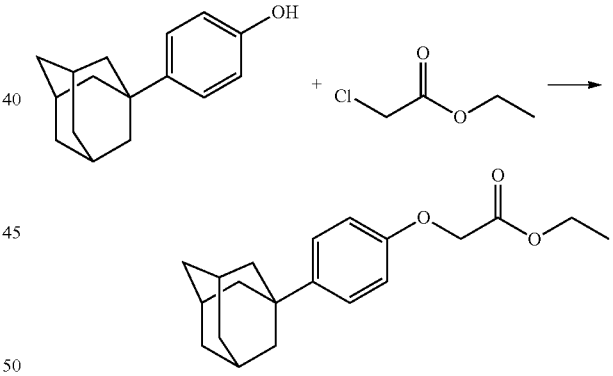

iv) The compound of Formula 2 can be prepared from the compound of Formula 9 by hydrolysis reaction with hydroxymetal compound (e.g. lithium hydroxide monohydrate) in mixture of tetrahydrofuran (THF) and $H_2O$. An example of the above reaction is illustrated below.

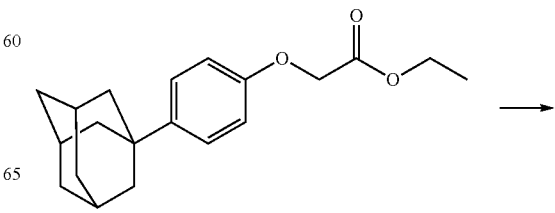

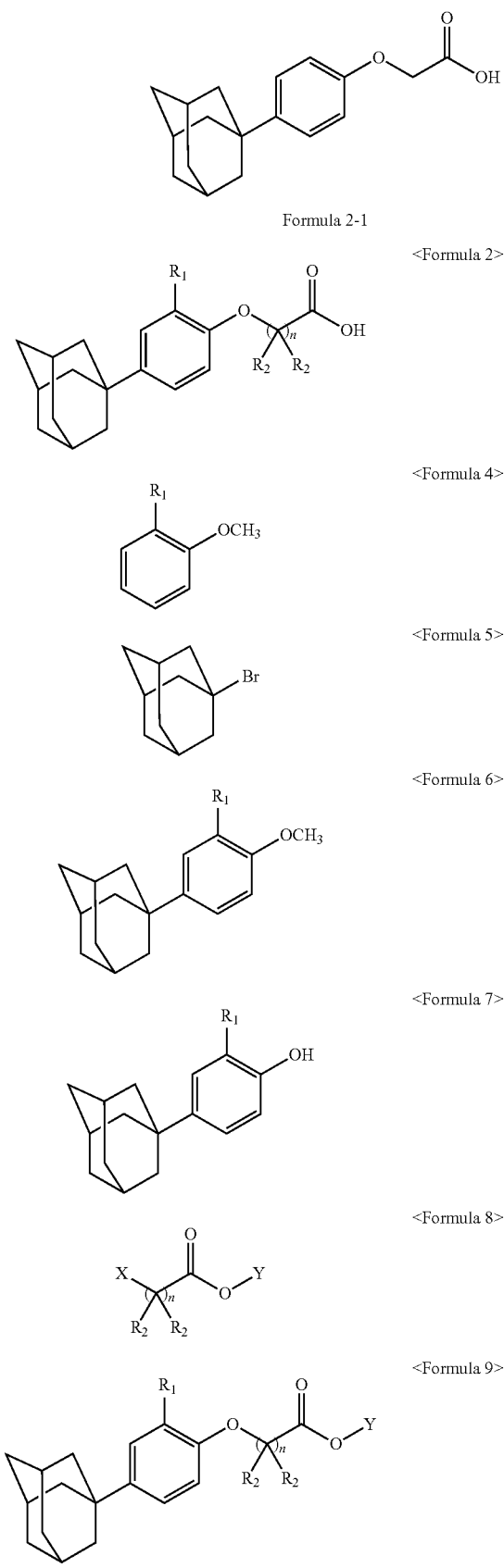

Formula 2-1

<Formula 2>

<Formula 4>

<Formula 5>

<Formula 6>

<Formula 7>

<Formula 8>

<Formula 9>

Wherein, $R_1$, $R_2$ and n are the same as defined in Formula I;

X represents chloro or bromo;

Y represents methyl or ethyl.

In addition, the present invention provides the derivative represented by Formula I, as used herein the pharmaceutically acceptable salts comprise base addition, acid addition and quaternary salts. The compounds of the present invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxylmethyl)aminomethane, L-arginine, L-lysine, N-ethylpiperidine, dibenzylamine and the like. The compounds of Formula I which are basic can form salts, including pharmaceutically acceptable salts with inorganic acids, e.g. with hydrohalic acids such as hydrorchloric or hydrobromic acids, sulfuric acid, nitric acid or phosphoric acid and the like, and with organic acids e.g. with acetic, tartaric, succinic, fumaric, maleic, malic, salicyclic, citric, succinic, trifluoroacetic, methanesulfonic, p-toluenesulfonic, benzoic, benzenesulfonic, glutamic, lactic, and mandelic acids and the like.

The acid addition salt can be achieved through usual method, for example, the compound Formula I dissolved in excess acid solution is deposited with water compatible organic solvent like methanol, ethanol, acetone or acetonitrile.

Also, the compound of Formula I in the present invention can be prepared for pharmaceutically acceptable metal salts with base. In detail, the alkaine metal or alkaline earth metal salt can be prepared following method. First, the compound is dissolved in excess alkaline metal hydroxide or alkaline earth metal hydroxide. Then, undissolved salts are filtered, and filtrates are dried after evaporating. The pharmaceutically suitable metal salts are the sodium, potassium or calcium salts.

Preferred examples of pharmaceutically acceptable salts of Formula I compounds according to the present invention comprise the followings:

4-(2-(4-Adamantan-1-yl)phenoxy)acetyl)-1-methylpiperazin-1-ium chloride (I-4);

4-(2-(4-(Adamantan-1-yl)phenoxy)acetyl)-1,1-dimethylpiperazine-1-ium iodide (I-15);

4-(2-(4-(Adamantan-1-yl)-2-methylphenoxy)acetyl)-1,1-dimethylpiperazin-1-ium iodide (I-16);

2-(2-(4-(Adamantan-1-yl)-2-methylphenoxy)acetamido)-N,N,N-trimethylethanaminium iodide (I-17);

4-(3-(4-(Adamantan-1-yl)phenoxy)propanoyl)-1,1-dimethylpiperazin-1-ium iodide (I-18);

2-(3-(4-(Adamantan-1-yl)phenoxy)propanamido)-N,N,N-trimethylethanaminium iodide (I-19);

4-(3-(4-(Adamantan-1-yl)-2-methylphenoxy)propanoyl)-1,1-dimethylpiperazin-1-ium iodide (I-20);

2-(3-(4-(Adamantan-1-yl)-2-methylphenoxy)propanamido)-N,N,N-trimethylethanaminium iodide (I-21);

4-(4-(4-(Adamantan-1-yl)phenoxy)butanoyl)-1,1-dimethylpiperazin-1-ium iodide (I-22);

4-(2-(4-(Adamantan-1-yl)phenoxy)acetyl)-1-methylpiperazin-1-ium methanesulfonate (I-43);

4-(2-(4-(Adamantan-1-yl)phenoxy)acetyl)-1-methylpiperazin-1-ium 3-carboxy-2-(carboxymethyl)-2-hydroxypropanoate (I-44);

4-(2-(4-(Adamantan-1-yl)phenoxy)acetyl)-1-methylpiperazin-1-ium (Z)-3-carboxyacrylate (I-45);

4-(2-(4-(Adamantan-1-yl)phenoxy)acetyl)-1-methylpiperazin-1-ium 4-methylbenzenesulfonate (I-46);

4-(2-(4-(Adamantan-1-yl)phenoxy)acetyl)-1-methylpiperazin-1-ium (2R,3R)-3-carboxy-2,3-dihydroxypropanoate (I-47);
4-(2-(4-(Adamantan-1-yl)phenoxy)acetyl)-1-methylpiperazin-1-ium 3-carboxypropanoate (I-48);
4-(2-(4-(Adamantan-1-yl)phenoxy)acetyl)-1-methylpiperazin-1-ium hydrogensulfate (I-49);
4-(2-(4-(Adamantan-1-yl)phenoxy)acetyl)-1-methylpiperazin-1-ium dihydrogenphosphate (I-50);
4-(2-(4-(Adamantan-1-yl)phenoxy)acetyl)-1-methylpiperazin-1-ium (E)-3-carboxyacrylate (I-51); and
4-(2-(4-(Adamantan-1-yl)phenoxy)acetyl)-1-methylpiperazin-1-ium trifluoroacetate (I-52).

In addition, the present invention relates to HIF-1α inhibitors comprising the compounds of above Formula I, pharmaceutically acceptable salts, solvates or hydrates thereof as effective components. The compounds according to the present invention that are developed as pharmaceutical agents comprise the compounds of Formula I, pharmaceutically acceptable salts, solvates or hydrates thereof.

The compounds according to the present invention can be considered as novel prevention and/or treatment for cancer, diabetic retinopathy, and rheumatoid arthritis by inhibiting HIF-1α-mediated gene expression. Therefore, the compounds according to the present invention exhibit anti-cancer activity not through nonselective cytotoxicity, but through selective inhibitory effects on activity of the transcription factor, HIF-1α, which plays a pivotal role in the growth and metastasis of cancer cells.

As used herein, the term "inhibitory activity against HIF-1α" of the compounds according to the present invention is intended to encompass all effects on suppressing the transcription of HRE (Hypoxia Responsive Element, 5'-ACGTG-3'), HIF-1α accumulation, and HIF-1α-mediated gene expression.

The effects of the compounds according to the present invention on the activation of HRE transcription mediated by HIF-1α under hypoxia were examined. As a result, the compounds potently inhibited HIF-1α-mediated transcriptional activity. Therefore, the compounds of the present invention can be used as active ingredients of anti-cancer agents, due to inhibitory effects on HIF-1α-mediated HRE transcription under hypoxia that suppress the growth and metastasis of cancer by down-regulating of the expression of oncogenes.

The compounds according to the present invention also inhibited the expression of HIF-1α proteins in a dose-dependent manner with no effects on β-actin expression under hypoxia. Therefore, the compounds according to the present invention can display anti-cancer activity without severe side effects, because the compounds suppressed the growth and metastasis of cancer cells by specifically inhibiting HIF-1α accumulation, rather than inducing nonspecific cell death.

Furthermore, the compounds according to the present invention show dose-dependent inhibitory activity against the expression of the HIF-1α target genes involved in the growth and metastasis of cancer, including VEGFA (Vascular endothelial growth factor A) that plays an important role in the growth and metastasis of cancer and EPO (erythropoietin) that promotes the generation of erythrocytes. Therefore, the compounds according to the present invention can be used as active ingredients for cancer treatment, due to decreased expression of several HIF-1α target genes such as VEGFA and EPO contributing to the growth and metastasis of cancer.

Hence, the compounds according to the present invention can effectively inhibit the activity of HIF-1α and are applicable to the prevention and/or treatment of various cancers comprising large intestine cancer, hepatic cancer, stomach cancer, breast cancer, colon cancer, bone cancer, pancreatic cancer, head or neck cancer, cervical cancer, ovarian cancer, rectal cancer, esophageal cancer, small intestine cancer, perianal cancer, fallopian tube cancer, endometrial cancer, uterine cervical cancer, vaginal cancer, vulvar cancer, Hodgikin's disease, prostatic cancer, bladder cancer, kidney cancer, ureter cancer, renal cell carcinoma, renal pelvis cancer, and central nervous system tumors.

Moreover, the compounds according to the present invention are therapeutically effective for diabetic retinopathy or rheumatoid arthritis by inhibitory activity against HIF-1α. The above term "inhibitory activity against HIF-1α" encompasses all effects on suppressing HRE (Hypoxia Responsive Element, 5'-ACGTG-3') transcription, HIF-1α accumulation, and HIF-1α-mediated gene expression. As mentioned above, the compounds according to the present invention can selectively inhibit the expression of VEGFA in hypoxia without influencing the expression of the control gene GAPDH. Accordingly, the compounds of the present invention are useful as effective components for the prevention and/or treatment of diabetic retinopathy or rheumatoid arthritis, because VEGFA genes can be expressed by HIF-1α under hypoxia.

The present invention also provides HIF-1α inhibitors comprising the compounds of Formula I, pharmaceutically acceptable salts, solvates or hydrates thereof as effective components. In addition, the present invention provides a pharmaceutical composition for the prevention and/or treatment of cancer, diabetic retinopathy or rheumatoid arthritis comprising the above HIF-1α inhibitors.

The present invention also provides a method of preventing and/or treating cancer, diabetic retinopathy or rheumatoid arthritis in a subject in need thereof, comprising administering an effective amount of a pharmaceutical composition comprising the above HIF-1α to the subject. The effective dosage of the composition of the present invention can be determined by those in the art according to weight and condition of a patient, severity of a disease, formulation of a drug, administration pathway and time. The above dosage cannot limit the scope of the invention in any way. Also, the pharmaceutical composition of the present invention may be administered to mammals comprising humans but is not limited thereto.

The pharmaceutical compositions according to the present invention can be formulated into oral or non-oral dosage forms. Examples of oral dosage forms include tablets, pills, hard/soft capsules, liquids, suspensions, emulsions, syrups, granules, elixirs, etc. These forms include diluents (for example, lactose, dextrose, sucrose, mannitol, sorbitol, cellulose, and/or glycin), and/or lubricants (for example, silica, talc, stearic acid or magnesium or calcium salts thereof, and/or polyethylene glycol) in addition to the effective components. Tablets include binders such as magnesium aluminum silicate, starch paste, gelatin, methyl cellulose, sodium carboxymethyl-cellulose and/or polyvinylpyrrolidone, and optionally disintegrants. Depending on cases, starch, agar, alginic acid or sodium salt thereof, a boiling mixture, and/or absorbents, colorants, flavoring agents, and sweeteners can be used.

Also, the pharmaceutical compositions according to the present invention can be administered via non-oral routes. For this, the composition can be formulated into subcutaneous, intravenous, intravenous, intramuscular, or intrathoracic injections. In order to obtain such non-oral dosage forms, the compounds according to the present invention are mixed with a stabilizer or a buffer in water to produce a solution or a suspension which is then packaged into ampule or vial units.

Furthermore, the above composition can contain a preservative, a stabilizer, a wettable agent, an emulsifier, an auxiliary agent, such as an osmotic pressure-controlling salt and a buffer, and/or other therapeutically effective materials. They can be mixed, granulized, or coated according to general methods.

The compounds according to the prevent invention can be administered once daily or in divided doses to mammals including humans, at a dose of 0.1 to 500 mg/kg (body weight) a day, and preferably at a dose of 0.5 to 100 mg/kg (body weight), via an oral or non-oral route.

The pharmaceutical composition of the present invention can be used alone or in combination with surgery, radiotherapy, hormone treatment, chemotherapy or a biological response regulator.

Advantageous Effects of Invention

The present invention relates to novel compounds inhibiting HIF-1α activity, preparation methods thereof, and HIF-1α inhibitors comprising the above compounds as effective components.

The compounds, HIF-1α inhibitors, according to the present invention can be new therapeutic options to develop treatment for various solid cancers such as colon, liver, gastric, and breast cancers. In addition, the compounds can be used as diabetic retinopathy and rheumatoid arthritis aggravated by up-regulation of HIF-1α-mediated VEGFA gene expression under hypoxia.

BEST MODE FOR CARRYING OUT THE INVENTION

Figure 1:
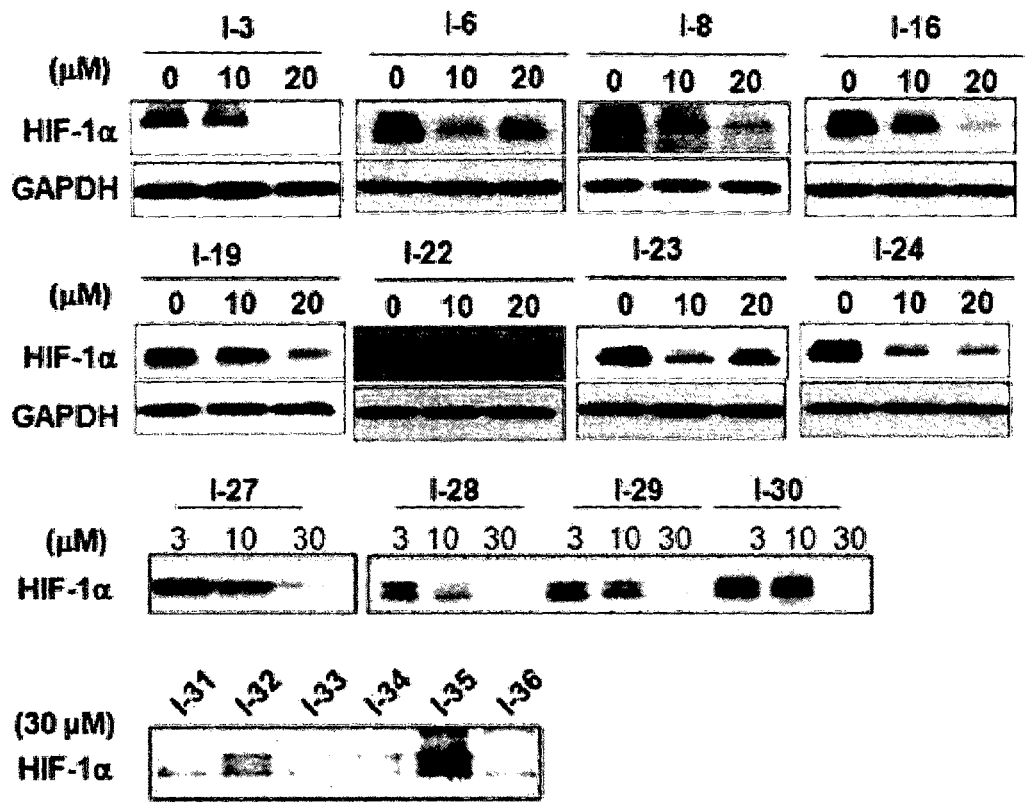
FIG. 1 shows the inhibitory activity of the compounds according to the present invention against HIF-1α expression.

The present invention will be described more particularly by the Examples but the present invention is not limited at all by these examples.

Example 1

2-(4-(Adamantan-1-yl)phenoxy)-N,N-dimethylacetamide (I-1)

A suspension of 2-(4-(adamantan-1-yl)phenoxy)acetic acid (0.2 g, 0.69 mmol), dimethylamine (0.031 g, 0.69 mmol), 1-ethyl-3-(3-dimethylaminopropyl)carbodiimide HCl (EDCI) (0.16 g, 0.83 mmol) and 1-hydroxybenzotriazole hydrate (HOBt) (0.11 g, 0.83 mmol) in N,N-dimethylformamide (2 mL) was added N,N-diisopropylethylamine (DIPEA) (0.106 mL, 1.74 mmol) and stirred at room temperature under nitrogen overnight. Reaction mixture was diluted with ethyl acetate and subsequentially washed with aqueous sodium hydroxide and brine. The organic layer was dried over anhydrous magnesium sulfate. The solvent was filtered and evaporated under reduced pressure to afford a crude solid, which was purified by silica gel column chromatography to give 2-(4-(adamantan-1-yl)phenoxy)-N,N-dimethylacetamide as a white solid (0.198 g, 90.3% yield).

$^1$H-NMR (DMSO-$d_6$, 500 MHz) δ 7.23 (2H, d, aromatic-H), 6.82 (2H, d, aromatic-H), 4.73 (2H, s, OCH$_2$), 2.98 (3H, s, CH$_3$), 2.83 (3H, s, CH$_3$), 2.03 (3H, brs, adamantyl-H), 1.82 (6H, m, adamantyl-H), 1.71 (6H, m, adamantyl-H).

Example 2

2-(4-(Adamantan-1-yl)phenoxy)-N-cyclopropylacetamide (I-2)

The title compound was prepared from 2-(4-(adamantan-1-yl)phenoxy)acetic acid (0.2 g, 0.69 mmol) and cyclopropylamine (0.039 g, 0.69 mmol) according to the example 1, which was given 2-(4-(adamantan-1-yl)phenoxy)-N-cyclopropylacetamide as a white solid (0.198 g, 87.4% yield).

$^1$H-NMR (DMSO-$d_6$, 500 MHz) δ 8.07 (1H, s, (C=O) NH), 7.25 (2H, d, aromatic-H), 6.85 (2H, d, aromatic-H), 4.38 (2H, s, OCH$_2$), 2.67 (1H, m, cyclopropyl), 2.03 (3H, brs, adamantyl-H), 1.82 (6H, m, adamantyl-H), 1.71 (6H, m, adamantyl-H), 0.61 (2H, m, cyclopropyl), 0.48 (2H, m, cyclopropyl).

Example 3

2-(4-(Adamantan-1-yl)phenoxy)-1-(4-piperazin-1-yl) ethanone (I-3)

The title compound was prepared from 2-(4-(adamantan-1-yl)phenoxy)acetic acid (2.0 g, 6.98 mmol) and 1-methylpiperazine (0.69 g, 6.98 mmol) according to the example 1, which was given 2-(4-(adamantan-1-yl)phenoxy)-1-(4-methylpiperazin-1-yl)ethanone as a white solid (2.4 g, 93.3% yield).

$^1$H-NMR (DMSO-$d_6$, 500 MHz) δ 7.23 (2H, d, aromatic-H), 6.82 (2H, d, aromatic-H), 4.74 (2H, s, OCH$_2$CO), 3.40 (4H, m, piperazine), 2.74 (4H, m, piperazine), 2.17 (3H, s, CH$_3$), 2.03 (3H, brs, adamantyl-H), 1.82 (6H, m, adamantyl-H), 1.71 (6H, m, adamantyl-H).

Example 4

4-(2-(4-(Adamantan-1-yl)phenoxy)acetyl)-1-methylpiperazin-1-ium chloride (I-4)

A suspension of 2-(4-(adamantan-1-yl)phenoxy)-1-(4-methylpiperazin-1-yl)ethanone (0.4 g, 1.08 mmol), prepared from example 3, and 1.0 M HCl solution in diethyl ether (0.047 g, 1.30 mmol) in diethyl ether (4 mL) was stirred at room temperature overnight. The reaction mixture was filtered and dried in vacuum to afford a 4-(2-(4-(adamantan-1-yl)phenoxy)acetyl)-1-methylpiperazin-1-ium chloride as a crystalline white solid (0.43 g, 97.9% yield).

$^1$H-NMR (DMSO-$d_6$, 500 MHz) δ 7.24 (2H, d, aromatic-H), 6.86 (2H, d, aromatic-H), 4.82 (2H, s, OCH$_2$CO), 4.20 (2H, m, piperazine), 3.38 (3H, m, piperazine), 3.05 (3H, m, piperazine), 2.77 (3H, s, CH$_3$), 2.04 (3H, brs, adamantyl-H), 1.82 (6H, m, adamantyl-H), 1.71 (6H, m, adamantyl-H).

Example 5

2-(4-(Adamantan-1-yl)-2-methylphenoxy)-1-(4-methylpiperazin-1-yl)ethanone (I-5)

Step 1: 1-(4-Methoxy-3-methylphenyl)adamantan

To a solution of 1-bromoadamantane (3.25 g, 15.25 mmol) and potassium carbonate (1.05 g, 7.62 mmol) in 1-methoxy- 2-methylbenzene (10 mL) was added 10 wt. % Pd/C (2.22 g) and stirred at 150° C. under nitrogen for 24 hours. The reaction mixture was cooled to room temperature and filtered. Solvent was evaporated under reduced pressure to afford a crude solid, which was purified by silica gel column chromatography to give 1-(4-methoxy-3-methylphenyl)adamantane as a white solid (4.9 g, 82.3% yield).

$^1$H-NMR (CDCl$_3$, 300 MHz) δ 7.15 (2H, m, aromatic-H), 6.78 (1H, d, aromatic-H), 3.81 (3H, s, OCH$_3$), 2.23 (3H, s, CH$_3$) 2.08 (3H, s, adamantyl-H), 1.90 (6H, m, adamantyl-H), 1.76 (6H, m, adamantyl-H).

Step 2: 4-(Adamantan-1-yl)-2-methylphenol 1-(4-methoxy-3-methylphenyl)adamantane was dissolved in dichloromethane (90 mL) and cooled to −10° C. Boron tribromide (BBr$_3$) (1.97 g, 8.31 mmol) was slowly added at −10° C. under nitrogen and stirred for 30 minutes at same temperature to 1.5 hours at room temperature. The reaction mixture was diluted with ethyl acetate and washed with brine. The organic layer was dried over anhydrous magnesium sulfate.

The solvent was filtered and evaporated under reduced pressure to afford a crude solid, which was purified by silica gel column chromatography to give 4-(Adamantan-1-yl)-2-methylphenol as a white solid (1.58 g, 100% yield).

$^1$H-NMR (CDCl$_3$, 300 MHz) δ 7.07 (2H, s, aromatic-H), 6.72 (1H, d, aromatic-H), 4.52 (1H, s, OH), 2.25 (3H, s, CH$_3$) 2.08 (3H, s, adamantyl-H), 1.88 (6H, m, adamantyl-H), 1.76 (6H, m, adamantyl-H).

Step 3: Ethyl 2-(4-(adamantan-1-yl)-2-methylphenoxy)acetate

To a solution of 4-(adamantan-1-yl)-2-methylphenol (2.0 g, 8.76 mmol) in N,N-dimethylformamide (10 mL) was added potassium carbonate (3.63 g, 23.29 mmol) and ethyl chloroacetate (1.29 g, 10.51 mmol), and stirred at room temperature overnight. The reaction mixture was diluted with ethyl acetate and washed with aqueous sodium bicarbonate. The organic layer was dried over anhydrous magnesium sulfate. The solvent was filtered and evaporated under reduced pressure to afford a crude solid, which was purified by silica gel column chromatography to give ethyl 2-(4-(adamantan-1-yl)-2-methylphenoxy)acetate as a white solid (2.6 g, 95.9% yield).

$^1$H-NMR (DMSO-d$_6$, 500 MHz) δ 7.06 (2H, m, aromatic-H), 6.72 (1H, m, aromatic-H), 4.73 (2H, s, OCH$_2$CO), 4.15 (2H, q, OCH$_2$CH$_3$), 2.18 (3H, q, CH$_3$), 2.03 (3H, brs, adamantyl-H), 1.81 (6H, m, adamantyl-H), 1.71 (6H, m, adamantyl-H), 1.2 (3H, t, CH$_3$).

Step 4: 2-(4-(Adamantan-1-yl)-2-methylphenoxy)acetic acid

To a solution of ethyl 2-(4-(adamantan-1-yl)-2-methylphenoxy)acetate (1.1 g, 3.50 mmol) in H$_2$O/THF (1 mL/1.20 mL) was added lithium hydroxide monohydrate (0.29 g, 7.00 mmol), and stirred at room temperature overnight. The reaction mixture was adjusted to acidic solution with 1 N aqueous HCl and extracted with dichloromethane. The organic layer was washed with H$_2$O and brine, and dried over anhydrous magnesium sulfate. The solvent was filtered and evaporated under reduced pressure to afford a crude solid, which was purified by silica gel column chromatography to give 2-(4-(adamantan-1-yl)-2-methylphenoxy)acetic acid as a white solid (0.54 g, 96.7% yield).

$^1$H-NMR (DMSO-d$_6$, 500 MHz) δ 12.91 (1H, bs, COOH), 7.13 (1H, s, aromatic-H), 7.05 (1H, m, aromatic-H), 6.70 (1H, d, aromatic-H), 4.63 (2H, s, OCH$_2$CO), 2.17 (3H, s, CH$_3$), 2.03 (3H, brs, adamantyl-H), 1.90 (6H, m, adamantyl-H), 1.76 (6H, m, adamantyl-H).

Step 5: 2-(4-(Adamantan-1-yl)-2-methylphenoxy)-1-(4-methylpiperazin-1-yl)ethanone The title compound was prepared from 2-(4-(adamantan-1-yl)-2-methylphenoxy)acetic acid (0.2 g, 0.66 mmol) and 1-methylpiperazine (0.06 g, 0.66 mmol) according to the example 1, which was given 2-(4-(adamantan-1-yl)-2-methylphenoxy)-1-(4-methylpiperazin-1-yl)ethanone as a white solid (0.23 g, 90.5% yield).

$^1$H-NMR (DMSO-d$_6$, 500 MHz) δ 7.12 (1H, m, aromatic-H), 7.05 (1H, m, aromatic-H), 6.74 (1H, m, aromatic-H), 4.74 (2H, s, OCH$_2$), 3.45 (4H, m, piperazine), 2.28 (4H, m, piperazine), 2.17 (6H, s, (CH$_3$)$_2$), 2.03 (3H, brs, adamantyl-H), 1.82 (6H, m, adamantyl-H), 1.71 (6H, m, adamantyl-H).

Example 6

2-(4-(Adamantan-1-yl)-2-methylphenoxy)-1-morpholinoethanone (I-6)

The title compound was prepared from 2-(4-(adamantan-1-yl)-2-methylphenoxy)acetic acid (0.2 g, 0.66 mmol), prepared from the step 4 of the example 5, and morpholine (0.058 g, 0.66 mmol) according to the example 1, which was given 2-(4-(adamantan-1-yl)-2-methylphenoxy)-1-morpholinoethanone as a white solid (0.228 g, 92.7% yield).

$^1$H-NMR (DMSO-d$_6$, 500 MHz) δ 7.12 (1H, s, aromatic-H), 7.04 (1H, m, aromatic-H), 6.76 (1H, d, aromatic-H), 4.77 (2H, t, OCH$_2$CH$_2$), 3.58 (4H, m, morpholine), 3.45 (4H, m, morpholine), 2.17 (3H, s, CH$_3$), 2.03 (3H, brs, adamantyl-H), 1.82 (6H, m, adamantyl-H), 1.71 (6H, m, adamantyl-H).

Example 7

2-(4-(Adamantan-1-yl)-2-methylphenoxy)-N-(2-(dimethylamino)ethyl)acetamide (I-7)

The title compound was prepared from 2-(4-(adamantan-1-yl)-2-methylphenoxy)acetic acid (0.2 g, 0.66 mmol), prepared from the step 4 of the example 5, and N,N-dimethylethane-1,2-diamine (0.058 g, 0.66 mmol) according to the example 1, which was given 2-(4-(adamantan-1-yl)-2-methylphenoxy)-N-(2-(dimethylamino)ethyl)acetamide as a white solid (0.22 g, 89.4% yield).

$^1$H-NMR (DMSO-d$_6$, 500 MHz) δ 7.73 (1H, t, (C=O)NH), 7.14 (1H, s, aromatic-H), 7.06 (1H, m, aromatic-H), 6.75 (1H, d, aromatic-H), 4.43 (2H, t, OCH$_2$CH$_2$), 3.22 (2H, m, NHCH$_2$CH$_2$), 2.50 (2H, m, NHCH$_2$CH$_2$), 2.30 (2H, t, OCH$_2$CH$_2$), 2.21 (3H, s, CH$_3$), 2.13 (6H, s, (CH$_3$)$_2$), 2.03 (3H, brs, adamantyl-H), 1.82 (6H, m, adamantyl-H), 1.71 (6H, m, adamantyl-H).

Example 8

3-(4-(Adamantan-1-yl)phenoxy)-1-(4-methylpiperazin-1-yl)propan-1-one (I-8)

The title compound was prepared from 3-(4-(adamantan-1-yl)phenoxy)propanoic acid (0.2 g, 0.66 mmol) and 1-methylpiperazine (0.06 g, 0.66 mmol) according to the example 1, which was given 3-(4-(adamantan-1-yl)phenoxy)-1-(4-methylpiperazin-1-yl)propan-1-one as a white solid (0.24 g, 94.4% yield).
$^1$H-NMR (DMSO-d$_6$, 500 MHz) δ 7.24 (2H, m, aromatic-H), 6.84 (2H, d, aromatic-H), 4.18 (2H, t, OCH$_2$CH$_2$), 3.85 (4H, m, piperazine), 3.39 (4H, m, piperazine), 3.16 (6H, s, (CH$_3$)$_2$), 2.86 (2H, t, CH$_2$CH$_2$), 2.03 (3H, brs, adamantyl-H), 1.82 (6H, m, adamantyl-H), 1.71 (6H, m, adamantyl-H).

Example 9

3-(4-(Adamantan-1-yl)phenoxy)-1-morpholinopropan-1-one (I-9)

The title compound was prepared from 3-(4-(adamantan-1-yl)phenoxy)propanoic acid (0.2 g, 0.66 mmol) and morpholine (0.058 g, 0.66 mmol) according to the example 1, which was given 3-(4-(adamantan-1-yl)phenoxy)-1-morpholinopropan-1-one as a white solid (0.23 g, 93.4% yield).
$^1$H-NMR (DMSO-d$_6$, 500 MHz) δ 7.24 (2H, d, aromatic-H), 6.84 (2H, d, aromatic-H), 4.16 (2H, t, OCH$_2$CH$_2$), 3.55 (4H, m, morpholine), 3.46 (4H, m, morpholine), 2.79 (2H, m, OCH$_2$CH$_2$), 2.03 (3H, brs, adamantyl-H), 1.82 (6H, m, adamantyl-H), 1.71 (6H, m, adamantyl-H).

Example 10

3-(4-(Adamantan-1-yl)phenoxy)-N-(2-(dimethylamino)ethyl)propanamide (I-10)

The title compound was prepared from 3-(4-(adamantan-1-yl)phenoxy)propanoic acid (0.2 g, 0.66 mmol) and N,N-dimethylethane-1,2-diamine (0.058 g, 0.66 mmol) according to the example 1, which was given 3-(4-(adamantan-1-yl)phenoxy)-N-(2-(dimethylamino)ethyl)propanamide as a white solid (0.225 g, 91.4% yield).
$^1$H-NMR (DMSO-d$_6$, 500 MHz) δ 7.88 (1H, t, (C=O)NH), 7.24 (2H, d, aromatic-H), 6.83 (2H, d, aromatic-H), 4.12 (2H, t, OCH$_2$CH$_2$), 3.14 (2H, m, NHCH$_2$CH$_2$), 2.5 (2H, m, NHCH$_2$CH$_2$), 2.28 (2H, t, OCH$_2$CH$_2$), 2.14 (6H, s, (CH$_3$)$_2$), 2.03 (3H, brs, adamantyl-H), 1.82 (6H, m, adamantyl-H), 1.71 (6H, m, adamantyl-H).

Example 11

3-(4-(Adamantan-1-yl)-2-methylphenoxy)-1-(4-methylpiperazin-1-yl)propan-1-one (I-11)

The title compound was prepared from 3-(4-(adamantan-1-yl)-2-methylphenoxy)propanoic acid (0.2 g, 0.63 mmol) and 1-methylpiperazine (0.063 g, 0.63 mmol) according to the example 1, which was given 3-(4-(adamantan-1-yl)-2-methylphenoxy)-1-(4-methylpiperazin-1-yl)propan-1-one as a white solid (0.236 g, 93.6% yield).
$^1$H-NMR (DMSO-d$_6$, 500 MHz) δ 7.08 (2H, m, aromatic-H), 6.84 (1H, d, aromatic-H), 4.15 (2H, t, OCH$_2$CH$_2$), 3.47 (4H, m, piperazine), 2.78 (2H, t, CH$_2$CH$_2$), 2.78 (1H, m, CH$_2$CH$_2$), 2.28 (4H, m, piperazine), 2.17 (3H, s, CH$_3$), 2.10 (3H, s, CH$_3$), 2.03 (3H, brs, adamantyl-H), 1.82 (6H, m, adamantyl-H), 1.71 (6H, m, adamantyl-H).

Example 12

3-(4-(Adamantan-1-yl)-2-methylphenoxy)-1-morpholinopropan-1-one (I-12)

The title compound was prepared from 3-(4-(adamantan-1-yl)-2-methylphenoxy)propanoic acid (0.2 g, 0.63 mmol) and morpholine (0.055 g, 0.63 mmol) according to the example 1, which was given 3-(4-(adamantan-1-yl)-2-methylphenoxy)-1-morpholinopropan-1-one as a white solid (0.22 g, 90.5% yield).
$^1$H-NMR (DMSO-d$_6$, 500 Hz) δ 7.10 (1H, s, aromatic-H), 7.07 (1H, d, aromatic-H), 6.84 (1H, d, aromatic-H), 4.16 (2H, t, OCH$_2$CH$_2$), 3.55 (4H, m, morpholine), 3.46 (4H, m, morpholine), 2.79 (2H, m, OCH$_2$CH$_2$), 2.09 (3H, s, CH$_3$), 2.03 (3H, brs, adamantyl-H), 1.82 (6H, m, adamantyl-H), 1.71 (6H, m, adamantyl-H).

Example 13

3-(4-(Adamantan-1-yl)-2-methylphenoxy)-N-(2-(dimethylamino)ethyl)propanamide (I-13)

The title compound was prepared from 3-(4-(adamantan-1-yl)-2-methylphenoxy)propanoic acid (0.2 g, 0.63 mmol) and N,N-dimethylethane-1,2-diamine (0.056 g, 0.63 mmol) according to the example 1, which was given 3-(4-(adamantan-1-yl)-2-methylphenoxy)-N-(2-(dimethylamino)ethyl)propanamide as a white solid (0.228 g, 93.4% yield).
$^1$H-NMR (DMSO-d$_6$, 500 MHz) δ 7.88 (1H, t, (C=O)NH), 7.08 (2H, t, aromatic-H), 6.83 (1H, d, aromatic-H), 4.12 (2H, t, OCH$_2$CH$_2$), 3.16 (2H, m, NHCH$_2$CH$_2$), 2.5 (2H, m, NHCH$_2$CH$_2$), 2.28 (2H, t, OCH$_2$CH$_2$), 2.13 (6H, s, (CH$_3$)$_2$), 2.09 (3H, s, CH$_3$), 2.03 (3H, brs, adamantyl-H), 1.82 (6H, m, adamantyl-H), 1.71 (6H, m, adamantyl-H).

Example 14

4-(4-(Adamantan-1-yl)phenoxy)-1-(4-methylpiperazin-1-yl)butan-1-one (I-14)

Step 1: Ethyl 4-(4-(adamantan-1-yl)phenoxy)butanoate

To a solution of 4-(adamantan-1-yl)phenol (2.0 g, 8.76 mmol) in N,N-dimethylformamide was added potassium carbonate (3.63 g, 26.29 mmol) and ethyl 4-bromobutanoate (1.29 g, 10.51 mmol), and stirred at room temperature overnight. The reaction mixture was diluted with ethyl acetate and washed with aqueous sodium bicarbonate. The organic layer was dried over anhydrous magnesium sulfate. The solvent was filtered and evaporated under reduced pressure to afford a crude solid, which was purified by silica gel column chromatography to give ethyl 4-(4-(adamantan-1-yl)phenoxy)butanoate as a white solid (2.7 g, 90% yield).
$^1$H-NMR (DMSO-d$_6$, 500 MHz) δ 7.23 (2H, d, aromatic-H), 6.83 (2H, d, aromatic-H), 4.06 (2H, q, CH$_2$CH$_3$), 3.94 (2H, t, (CH$_2$)$_3$), 2.43 (2H, t, (CH$_2$)$_3$), 2.08 (3H, s, adamantyl-H), 1.92 (2H, m, (CH$_2$)$_3$), 1.88 (6H, m, adamantyl-H), 1.76 (6H, m, adamantyl-H), 1.17 (3H, m, CH$_3$).

Step 2: 4-(4-(Adamantan-1-yl)phenoxy)butanoic acid

To a solution of ethyl 4-(4-(adamantan-1-yl)phenoxy)butanoate (1.1 g, 3.50 mmol) in H$_2$O/THF (1 mL/1.20 mL) was added lithium hydroxide monohydrate (0.14 g, 7.00 mmol), and stirred at room temperature overnight. The reaction mixture was adjusted to acidic solution with 1 N aqueous HCl and extracted with dichloromethane. The organic layer was washed with H$_2$O and brine, and dried over anhydrous magnesium sulfate. The solvent was filtered and evaporated under reduced pressure to afford a crude solid, which was purified by silica gel column chromatography to give 4-(4-(adamantan-1-yl)phenoxy)butanoic acid as a white solid (0.98 g, 97.12% yield).

$^1$H-NMR (DMSO-$d_6$, 500 MHz) δ 12.11 (1H, bs, COOH), 7.23 (2H, d, aromatic-H), 6.83 (2H, d, aromatic-H), 3.93 (2H, t, (CH$_2$)$_3$), 2.36 (2H, t, (CH$_2$)$_3$), 2.03 (3H, s, adamantyl-H), 1.91 (2H, m, (CH$_2$)$_3$), 1.81 (6H, m, adamantyl-H), 1.71 (6H, m, adamantyl-H).

Step 3: 4(-(4-(Adamantan-1-yl)phenoxy)-1-(4-methylpiperazin-1-yl)butan-1-one (I-14)

The title compound was prepared from 4-(4-(adamantan-1-yl)phenoxy)butanoic acid (0.2 g, 0.63 mmol) and 1-methylpiperazine (0.063 g, 0.63 mmol) according to the example 1, which was given 4-(4-(adamantan-1-yl)phenoxy)-1-(4-methylpiperazin-1-yl)butan-1-one as a white solid (0.239 g, 95.0% yield).

$^1$H-NMR (DMSO-$d_6$, 500 MHz) δ 7.23 (2H, d, aromatic-H), 6.83 (2H, d, aromatic-H), 3.94 (2H, t, OCH$_2$(CH$_2$)$_2$), 3.42 (4H, m, piperazine), 2.43 (2H, m, CH$_2$(CH$_2$)$_2$), 2.22 (4H, m, piperazine), 2.15 (3H, s, CH$_3$), 2.03 (3H, brs, adamantyl-H), 1.90 (2H, m, CH$_2$(CH$_2$)$_2$), 1.82 (6H, m, adamantyl-H), 1.71 (6H, m, adamantyl-H).

Example 15

4-(2-(4-Adamantan-1-yl)phenoxy)acetyl)-1,1-dimethylpiperazin-1-ium iodide (I-15)

A suspension of 2-(4-(Adamantan-1-yl)phenoxy)-1-(4-methylpiperazin-1-yl)ethanone (0.2 g, 0.50 mmol), prepared from example 3, and methyl iodide (0.286 g, 2.01 mmol) in diethyl ether (2 mL) was stirred at room temperature overnight. The reaction mixture was filtered and dried in vacuum oven at 50° C. to afford a 4-(2-(4-(adamantan-1-yl)phenoxy)acetyl)-1,1-dimethylpiperazin-1-ium iodide as a white solid (0.27 g, 97.5% yield).

$^1$H-NMR (DMSO-$d_6$, 500 Hz) δ 7.24 (2H, d, aromatic-H), 6.85 (2H, d, aromatic-H), 4.74 (1H, s, OCH$_2$CO), 3.82 (1H, s, OCH$_2$CO), 3.43 (4H, m, piperazine), 3.16 (3H, s, CH$_3$), 2.27 (4H, m, piperazine), 2.17 (3H, s, CH$_3$), 2.03 (3H, brs, adamantyl-H), 1.82 (6H, m, adamantyl-H), 1.71 (6H, m, adamantyl-H).

Example 16

4-(2-(4-(Adamantan-1-yl)-2-methylphenoxy)acetyl)-1,1-dimethylpiperazin-1-ium iodide (I-16)

The title compound was prepared from 2-(4-(adamantan-1-yl)-2-methylphenoxy)-1-(4-methylpiperazin-1-yl)ethanone (0.2 g, 0.50 mmol), prepared from the example 5, according to the example 15, which was given 4-(2-(4-(adamantan-1-yl)-2-methylphenoxy)acetyl)-1,1-dimethylpiperazin-1-ium iodide as a white solid (0.268 g, 97.8% yield).

$^1$H-NMR (DMSO-$d_6$, 500 MHz) δ 7.12 (1H, m, aromatic-H), 7.05 (1H, m, aromatic-H), 6.74 (1H, d, aromatic-H), 4.84 (1H, s, OCH$_2$), 4.74 (1H, s, OCH$_2$), 3.83 (2H, m, piperazine), 3.40 (4H, m, piperazine), 3.17 (3H, s, CH$_3$), 2.25 (2H, m, piperazine), 2.17 (6H, d, (CH$_3$)$_2$), 2.03 (3H, brs, adamantyl-H), 1.82 (6H, m, adamantyl-H), 1.71 (6H, m, adamantyl-H).

Example 17

2-(2-(4-Adamantan-1-yl)-2-methylphenoxy)acetamido)-N,N,N-trimethylethanaminium iodide (I-17)

The title compound was prepared from 2-(4-(adamantan-1-yl)-2-methylphenoxy)-N-(2-(dimethylamino)ethyl)acetamide (0.2 g, 0.50 mmol), prepared from the example 7, according to the example 15, which was given 2-(2-(4-(adamantan-1-yl)-2-methylphenoxy)acetamido)-N,N,N-trimethylethaneaminium iodide as a white solid (0.27 g, 97.8% yield).

$^1$H-NMR (DMSO-$d_6$, 500 MHz) δ 8.16 (1H, t, (C=O) NH), 7.15 (1H, s, aromatic-H), 7.06 (1H, m, aromatic-H), 6.75 (1H, d, aromatic-H), 4.50 (2H, t, OCH$_2$CH$_2$), 3.57 (2H, m, NHCH$_2$CH$_2$), 3.40 (2H, t, NHCH$_2$CH$_2$), 3.07 (6H, s, (CH$_3$)$_2$), 2.50 (2H, t, OCH$_2$CH$_2$), 2.23 (3H, s, CH$_3$), 2.03 (3H, brs, adamantyl-H), 1.82 (6H, m, adamantyl-H), 1.71 (6H, m, adamantyl-H).

Example 18

4-(3-(4-(Adamantan-1-yl)phenoxy)propanoyl-1,1-dimethylpiperazin-1-ium iodide (I-18)

The title compound was prepared from 3-(4-(adamantan-1-yl)phenoxy)-1-(4-methylpiperazin-1-yl)propan-1-one (0.2 g, 0.50 mmol), prepared from the example 8, according to the example 15, which was given 4-(3-(4-(adamantan-1-yl)phenoxy)propanoyl-1,1-dimethylpiperazin-1-ium iodide as a white solid (0.266 g, 97.0% yield).

$^1$H-NMR (DMSO-$d_6$, 500 MHz) δ 7.24 (2H, m, aromatic-H), 6.84 (2H, d, aromatic-H), 4.15 (2H, t, OCH$_2$CH$_2$), 3.45 (4H, m, piperazine), 2.77 (2H t, CH$_2$CH$_2$), 2.28 (4H, m, piperazine), 2.17 (3H, s, CH$_3$), 2.03 (3H, brs, adamantyl-H), 1.82 (6H, m, adamantyl-H), 1.71 (6H, m, adamantyl-H).

Example 19

2-(3-(4-(Adamantan-1-yl)phenoxy)propanamido)-N,N,N-trimethylethanaminium iodide (I-19)

The title compound was prepared from 3-(4-(adamantan-1-yl)phenoxy)-N-(2-(dimethylamino)ethyl)propanamide (0.2 g, 0.50 mmol), prepared from the example 10, according to the example 15, which was given 2-(3-(4-(adamantan-1-yl)phenoxy)propanamido)-N,N,N-trimethylethaneaminium iodide as a white solid (0.265 g, 96.0% yield).

$^1$H-NMR (DMSO-$d_6$, 500 MHz) δ 8.32 (1H, t, (C=O) NH), 7.24 (2H, d, aromatic-H), 6.83 (2H, d, aromatic-H), 4.15 (2H, t, OCH$_2$CH$_2$), 3.51 (2H, m, NHCH$_2$CH$_2$), 3.37 (2H, m, NHCH$_2$CH$_2$), 3.09 (9H, s, (CH$_3$)$_3$), 2.55 (2H, t, OCH$_2$CH$_2$), 2.03 (3H, brs, adamantyl-H), 1.82 (6H, m, adamantyl-H), 1.71 (6H, m, adamantyl-H).

Example 20

4-(3-(4-(Adamantan-1-yl)-2-methylphenoxy)propanoyl)-1,1-dimethylpiperazin-1-ium iodide (I-20)

The title compound was prepared from 3-(4-(adamantan-1-yl)-2-methylphenoxy)-1-(4-methylpiperazin-1-yl)propan-1-one (0.2 g, 0.50 mmol), prepared from the example 11, according to the example 15, which was given 4-(3-(4-(adamantan-1-yl)-2-methylphenoxy)propanoyl)-1,1-dimethylpiperazin-ium iodide as a white solid (0.261 g, 96.3% yield).

$^1$H-NMR (DMSO-$d_6$, 500 MHz) δ 7.08 (2H, m, aromatic-H), 6.84 (1H, d, aromatic-H), 4.16 (2H, t, OCH$_2$CH$_2$), 3.84 (2H, m, piperazine), 3.46 (4H, m, piperazine) 3.37 (1H, m, CH$_2$CH$_2$), 2.78 (1H, m, CH$_2$CH$_2$), 3.15 (3H, s, CH$_3$), 2.28 (2H, m, piperazine), 2.10 (3H, s, (CH$_3$)$_2$), 2.03 (3H, brs, adamantyl-H), 1.82 (6H, m, adamantyl-H), 1.71 (6H, m, adamantyl-H).

Example 21

2-(3-(4-Adamantan-1-yl)-2-methylphenoxy)propanamido)-N,N,N-trimethylethanaminium iodide (I-21)

The title compound was prepared from 3-(4-(adamantan-1-yl)-2-methylphenoxy)-N-(2-(dimethylamino)ethyl)propanamide (0.2 g, 0.50 mmol), prepared from the example 13, according to the example 15, which was given 2-(3-(4-(adamantan-1-yl)-2-methylphenoxy)propanamido)-N,N,N-trimethylethaneaminium iodide as a white solid (0.269 g, 98.5% yield).

$^1$H-NMR (DMSO-$d_6$, 500 MHz) δ 8.31 (1H, t, (C=O)NH), 7.08 (2H, t, aromatic-H), 6.83 (1H, d, aromatic-H), 4.15 (2H, t, OCH$_2$CH$_2$), 3.51 (2H, m, NHCH$_2$CH$_2$), 3.36 (2H, m, NHCH$_2$CH$_2$), 3.09 (9H, s, (CH$_3$)$_3$), 2.57 (2H, t, OCH$_2$CH$_2$), 2.09 (3H, s, CH$_3$), 2.03 (3H, brs, adamantyl-H), 1.82 (6H, m, adamantyl-H), 1.71 (6H, m, adamantyl-H).

Example 22

4-(4-(4-(Adamantan-1-yl)phenoxy)butanoyl)-1,1-dimethylpiperazin-1-ium iodide (I-22)

The title compound was prepared from 4-(4-(adamantan-1-yl)phenoxy)-1-(4-methylpiperazin-1-yl)butan-1-one (0.2 g, 0.50 mmol), prepared from the example 14, according to the example 15, which was given 4-(4-(4-(adamantan-1-yl)phenoxy)butanoyl)-1,1-dimethylpiperazin-1-ium iodide as a white solid (0.265 g, 97.7% yield).

$^1$H-NMR (DMSO-$d_6$, 500 MHz) δ 7.23 (2H, d, aromatic-H), 6.83 (2H, d, aromatic-H), 3.95 (2H, t, OCH$_2$(CH$_2$)$_2$), 3.80 (4H, m, piperazine), 3.36 (4H, m, piperazine), 3.14 (6H, s, (CH$_3$)$_2$), 2.53 (2H, m, CH$_2$(CH$_2$)$_2$), 2.04 (2H, m, CH$_2$(CH$_2$)$_2$), 2.03 (3H, brs, adamantyl-H), 1.82 (6H, m, adamantyl-H), 1.71 (6H, m, adamantyl-H).

Example 23

2-(4-(Adamantan-1-yl)phenoxy)-2-methyl-1-(4-methylpiperazin-1-yl)propan-1-one (I-23)

Step 1: Methyl 2-(4-(adamantan-1-yl)phenoxy-2-methylpropanoate

To a solution of 4-(adamantan-1-yl)phenol (0.8 g, 3.50 mmol) in N,N-dimethylformamide (8 mL) was added anhydrous potassium carbonate (1.45 g, 10.51 mmol) and methyl 2-bromo-2-methylpropanoate (1.15 g, 7.0 mmol), and stirred at room temperature for 12 hours. The reaction mixture was diluted with ethyl acetate and washed with aqueous sodium bicarbonate. The organic layer was dried over anhydrous magnesium sulfate. The solvent was filtered and evaporated under reduced pressure to afford a crude solid, which was purified by silica gel column chromatography to give methyl 2-(4-(adamantan-1-yl)phenoxy)-2-methylpropanoate as colorless oil (1.1 g, 94.1% yield).

$^1$H-NMR (MeOH-$d_4$, 500 MHz) δ 7.21 (2H, d, aromatic-H), 6.75 (2H, d, aromatic-H), 3.73 (3H, s, OCH$_3$), 2.05 (3H, brs, adamantyl-H), 1.88 (6H, m, adamantyl-H), 1.77 (6H, m, adamantyl-H), 1.52 (6H, s, (CH$_3$)$_2$).

Step 2: 2-(4-(Adamantan-1-yl)phenoxy)-2-methylpropanoic acid

To a solution of methyl 2-(4-(adamantan-1-yl)phenoxy)-2-methylpropanoate (1.0 g, 3.00 mmol), prepared from step 1, in H$_2$O/THF (1:1.20 mL) was added lithium hydroxide monohydrate (0.51 g, 12.00 mmol), and stirred at room temperature overnight. The reaction mixture was adjusted to acidic solution with 1 N aqueous HCl and extracted with dichloromethane. The organic layer was washed with H$_2$O and brine, and dried over anhydrous magnesium sulfate. The solvent was filtered and evaporated under reduced pressure to afford a crude solid, which was purified by silica gel column chromatography to give 2-(4-(adamantan-1-yl)phenoxy)-2-methylpropanoic acid as a white solid (0.92 g, 96.1% yield).

$^1$H-NMR (DMSO-$d_6$, 500 MHz) δ 12.94 (1H, bs, COOH), 7.23 (2H, d, aromatic-H), 6.74 (2H, d, aromatic-H), 2.03 (3H, brs, adamantyl-H), 1.81 (6H, m, adamantyl-H), 1.71 (6H, m, adamantyl-H), 1.47 (6H, s, (CH$_3$)$_2$).

Step 3: 2-(4-(Adamantan-1-yl)phenoxy)-2-methyl-1-(4-methylpiperazin-1-yl)propan-1-one The title compound was prepared from 2-(4-(adamantan-1-yl)phenoxy)-2-methylpropanoic acid (0.2 g, 0.63 mmol) and 1-methylpiperazine (0.063 g, 0.63 mmol) according to the example 1, which was given 2-(4-(adamantan-1-yl)phenoxy)-2-methyl-1-(4-methylpiperazin-1-yl)propan-1-one as a white solid (0.236 g, 93.7% yield).

$^1$H-NMR (DMSO-$d_6$, 500 MHz) δ 7.23 (2H, d, aromatic-H), 6.71 (2H, d, aromatic-H), 3.71 (2H, bs, piperazine), 3.47 (2H, bs, piperazine), 2.13 (2H, bs, piperazine), 2.03 (3H, brs, adamantyl-H), 1.99 (3H, s, CH$_3$), 1.83 (2H, bs, piperazine), 1.81 (6H, m, adamantyl-H), 1.68 (6H, m, adamantyl-H), 1.47 (6H, s, (CH$_3$)$_2$).

Example 24

2-(4-(Adamantan-1-yl)phenoxy)-N-(2-(dimethylamino)ethyl)-2-methylpropanamide (I-24)

The title compound was prepared from 2-(4-(adamantan-1-yl)phenoxy)-2-methylpropanoic acid (0.2 g, 0.63 mmol), prepared from the step 2 of example 23, and N,N-dimethylethane-1,2-diamine (0.056 g, 0.63 mmol) according to the example 1, which was given 2-(4-(adamantan-1-yl)phenoxy)-N-(2-(dimethylamino)ethyl)-2-methylpropanamide as a white solid (0.228 g, 93.4% yield).

$^1$H-NMR (DMSO-$d_6$, 500 MHz) δ 7.83 (1H, t, (C=O)NH), 7.23 (2H, d, aromatic-H), 6.83 (2H, d, aromatic-H), 4.08 (2H, m, NHCH$_2$CH$_2$), 2.26 (2H, t, NHCH$_2$CH$_2$), 2.12 (6H, s, (CH$_3$)$_2$), 2.03 (3H, brs, adamantyl-H), 1.82 (6H, m, adamantyl-H), 1.71 (6H, m, adamantyl-H), 1.47 (6H, s, (CH$_3$)$_2$).

Example 25

2-(4-(Adamantan-1-yl)-2-fluorophenoxy)-1-(4-methylpiperazin-1-yl)ethanone (I-25)

Step 1: 1-(3-Fluoro-4-methoxyphenyl)adamantane

The title compound was prepared from 1-fluoro-2-methoxybenzene (10 mL) and 1-bromoadamantane (3.25 g, 15.25 mmol) according to the step 1 of the example 5, which was given 1-(3-fluoro-4-methoxyphenyl)adamantane (5.05 g, 83.3% yield).

$^1$H-NMR (DMSO-$d_6$, 500 MHz) δ 7.25 (2H, m, aromatic-H), 6.78 (1H, d, aromatic-H), 3.82 (3H, s, OCH$_3$), 2.03 (3H, s, adamantyl-H), 1.80 (6H, m, adamantyl-H), 1.71 (6H, m, adamantyl-H).

Step 2: 4-(Adamantan-1-yl)-2-fluorophenol

The title compound was prepared from 1-(3-fluoro-4-methoxyphenyl)adamantane (3.0 g, 11.52 mmol) according to the step 2 of the example 5, which was given 4-(adamantan-1-yl)-2-fluorophenol (2.80 g, 99% yield).

$^1$H-NMR (DMSO-$d_6$, 500 MHz) δ 9.50 (1H, bs, COOH), 7.02 (2H, m, aromatic-H), 6.85 (1H, m, aromatic-H), 2.02 (3H, s, adamantyl-H), 1.78 (6H, m, adamantyl-H), 1.70 (6H, m, adamantyl-H).

Step 3: Ethyl 2-(4-(adamantan-1-yl)-2-fluorophenoxy)acetate

The title compound was prepared from 4-(adamantan-1-yl)-2-fluorophenol (2.0 g, 8.11 mmol), prepared from the step 2, according to the step 3 of the example 5, which was given ethyl 2-(4-(adamantan-1-yl)-2-fluorophenoxy)acetate (2.54 g, 94.8% yield).

$^1$H-NMR (DMSO-$d_6$, 500 MHz) δ 7.06 (2H, m, aromatic-H), 6.98 (1H, m, aromatic-H), 4.81 (2H, s, OCH$_2$CO), 4.15 (2H, q, OCH$_2$CH$_3$), 2.03 (3H, brs, adamantyl-H), 1.81 (6H, m, adamantyl-H), 1.71 (6H, m, adamantyl-H), 1.20 (3H, t, CH$_3$).

Step 4: 2-(4-(Adamantan-1-yl)-2-fluorophenoxy)acetic acid

The title compound was prepared from ethyl 2-(4-(adamantan-1-yl)-2-fluorophenoxy)acetate (1.1 g, 3.30 mmol), prepared from the step 3, according to the step 4 of the example 5, which was given 2-(4-(adamantan-1-yl)-2-fluorophenoxy)acetic acid (0.92 g, 91.3% yield).

$^1$H-NMR (DMSO-$d_6$, 500 MHz) δ 13.05 (1H, brs, COOH), 7.18 (1H, m, aromatic-H), 7.04 (1H, m, aromatic-H), 6.96 (1H, m, aromatic-H), 4.71 (2H, s, OCH$_2$CO), 2.03 (3H, brs, adamantyl-H), 1.81 (6H, m, adamantyl-H), 1.71 (6H, m, adamantyl-H).

Step 5: 2-(4-(Adamantan-1-yl)-2-fluorophenoxy)-1-(4-methylpiperazin-1-yl)ethanone (I-25)

The title compound was prepared from 2-(4-(adamantan-1-yl)-2-fluorophenoxy)acetic acid (0.15 g, 0.49 mmol), prepared from the step 4, and 1-methylpiperazine (0.049 g, 0.49 mmol) according to the example 1, which was given 2-(4-(adamantan-1-yl)-2-fluorophenoxy)-1-(4-methylpiperazin-1-yl)ethanone as a white solid (0.173 g, 91.3% yield).

$^1$H-NMR (DMSO-$d_6$, 500 MHz) δ 7.14 (1H, m, aromatic-H), 7.04 (1H, d, aromatic-H), 6.96 (1H, m, aromatic-H), 4.86 (2H, s, OCH$_2$CO), 3.43 (4H, m, piperazine), 2.25 (4H, m, piperazine), 2.18 (3H, s, CH$_3$), 2.03 (3H, brs, adamantyl-H), 1.81 (6H, m, adamantyl-H), 1.70 (6H, m, adamantyl-H).

Example 26

2-(4-(Adamantan-1-yl)phenoxy)-N-(furan-2-ylmethyl)acetamide (I-26)

The title compound was prepared from 2-(4-(adamantan-1-yl)phenoxy)acetic acid (0.3 g, 1.04 mmol) and furan-2-ylmethaneamine (0.101 g, 1.04 mmol) according to the example 1, which was given 2-(4-(adamantan-1-yl)phenoxy)-N-(furan-2-ylmethyl)acetamide as a white solid (0.346 g, 90.8% yield).

$^1$H-NMR (DMSO-$d_6$, 500 MHz) δ 8.52 (1H, t, (C=O)NH), 7.55 (1H, s, aromatic-H), 7.25 (2H, d, aromatic-H), 6.88 (2H, d, aromatic-H), 6.37 (1H, m, aromatic-H), 6.18 (1H, m, aromatic-H), 4.47 (2H, s, OCH$_2$CO), 4.32 (2H, s, CH$_2$), 2.04 (3H, brs, adamantyl-H), 1.82 (6H, m, adamantyl-H), 1.71 (6H, m, adamantyl-H).

Example 27

2-(4-(Adamantan-1-yl)phenoxy)-1-(4-(4-(trifluoromethyl)benzyl)piperazin-1-yl)ethanone (I-27)

The title compound was prepared from 2-(4-(adamantan-1-yl)phenoxy)acetic acid (0.3 g, 1.04 mmol) and 1-(4-(trifluoromethyl)benzyl)piperazine (0.255 g, 1.04 mmol) according to the example 1, which was given 2-(4-(adamantan-1-yl)phenoxy)-1-(4-(4-(trifluoromethyl)benzyl)piperazin-1-yl)ethanone as a white solid (0.501 g, 93.3% yield).

$^1$H-NMR (DMSO-$d_6$, 500 MHz) δ 7.70 (2H, d, aromatic-H), 7.55 (2H, d, aromatic-H), 7.23 (2H, d, aromatic-H), 6.82 (2H, d, aromatic-H), 4.74 (2H, s, OCH$_2$CH$_2$), 3.60 (2H, s, CH$_2$), 3.46 (4H, m, piperazine), 2.38 (4H, m, piperazine), 2.03 (3H, brs, adamantyl-H), 1.82 (6H, m, adamantyl-H), 1.71 (6H, m, adamantyl-H).

Example 28

2-(4-(Adamantan-1-yl)phenoxy)-1-(4-isopropylpiperazin-1-yl)ethanone (I-28)

The title compound was prepared from 2-(4-(adamantan-1-yl)phenoxy)acetic acid (0.23 g, 0.80 mmol) and 1-isopropylpiperazine (0.102 g, 0.80 mmol) according to the example 1, which was given 2-(4-(adamantan-1-yl)phenoxy)-1-(4-isopropylpiperazin-1-yl)ethanone as a white solid (0.298 g, 93.7% yield).

$^1$H-NMR (MeOH-$d_4$, 500 MHz) δ 7.18 (2H, d, aromatic-H), 6.78 (2H, d, aromatic-H), 4.65 (2H, s, OCH$_2$CO), 3.50 (4H, m, piperazine), 2.61 (1H, m, CH), 2.44 (4H, m, piperazine), 1.96 (3H, brs, adamantyl-H), 1.80 (6H, m, adamantyl-H), 1.69 (6H, m, adamantyl-H), 0.96 (6H, d, CH$_3$).

Example 29 tert-Butyl 4-(2-(4-(adamantan-1-yl)phenoxy)acetyl)piperazine-1-carboxylate (I-29)

The title compound was prepared from 2-(4-(adamantan-1-yl)phenoxy)acetic acid (0.28 g, 0.97 mmol) and tert-butyl piperazine-1-carboxylate (0.182 g, 0.97 mmol) according to the example 1, which was given tert-butyl 4-(2-(4-(adamantan-1-yl)phenoxy)acetyl)piperazine-1-carboxylate as a white solid (0.399 g, 90.0% yield).

$^1$H-NMR (MeOH-$d_4$, 500 MHz) δ 7.18 (2H, d, aromatic-H), 6.79 (2H, d, aromatic-H), 4.67 (2H, s, OCH$_2$CO), 3.47 (4H, m, piperazine), 3.35 (4H, m, piperazine), 1.96 (3H, brs, adamantyl-H), 1.80 (6H, m, adamantyl-H), 1.69 (6H, m, adamantyl-H), 1.36 (9H, s, (CH$_3$)$_3$).

Example 30

2-(4-(Adamantan-1-yl)phenoxy)-1-(piperazin-1-yl)ethanone (I-30)

To a solution of tert-butyl 4-(2-(4-(adamantan-1-yl)phenoxy)acetyl)piperazine-1-carboxylate (0.15 g, 0.42 mmol), prepared from the example 29, in dichloromethane (1.5 mL) was added trifluoroacetic acid (0.15 g, 1.69 mmol) and stirred at room temperature overnight. The reaction mixture was concentrated and diluted with dichloromethane. The organic layer was washed with aqueous sodium bicarbonate and dried over anhydrous magnesium sulfate. The solvent was filtered and evaporated under reduced pressure to afford a crude solid, which was purified by silica gel column chromatography to give 2-(4-(adamantan-1-yl)phenoxy)-1-(piperazin-1-yl) ethanone as a white solid (0.11 g, 94.8% yield).

$^1$H-NMR (MeOH-d$_4$, 500 MHz) δ 7.18 (2H, d, aromatic-H), 6.79 (2H, d, aromatic-H), 4.66 (2H, s, OCH$_2$CO), 3.52 (4H, m, piperazine), 2.80 (4H, m, piperazine), 1.96 (3H, brs, adamantyl-H), 1.80 (6H, m, adamantyl-H), 1.69 (6H, m, adamantyl-H).

Example 31

(S)-tert-Butyl 4-(2-(4-(adamantan-1-yl)phenoxy) acetyl)-3-methylpiperazine-1-carboxylate (I-31)

The title compound was prepared from 2-(4-(adamantan-1-yl)phenoxy)acetic acid (0.2 g, 0.69 mmol) and (S)-tert-butyl 3-methylpiperazine-1-carboxylate (0.139 g, 0.69 mmol) according to the example 1, which was given (S)-tert-butyl 4-(2-(4-(adamantan-1-yl)phenoxy)acetyl)-3-methylpiperazine-1-carboxylate as a white solid (0.298 g, 91.2% yield).

$^1$H-NMR (DMSO-d$_6$, 400 MHz) δ 7.30 (2H, d, aromatic-H), 6.89 (2H, d, aromatic-H), 4.84 (2H, s, OCH$_2$CO), 4.54 (1H, m, piperazine), 4.12 (2H, m, piperazine), 3.90 (2H, m, piperazine), 2.98 (2H, m, piperazine), 2.48 (3H, d, CH$_3$), 2.14 (3H, brs, adamantyl-H), 1.89 (6H, m, adamantyl-H), 1.78 (6H, m, adamantyl-H), 1.47 (9H, s, (CH$_3$)$_3$).

Example 32

2-(4-(Adamantan-1-yl)phenoxy)-1-((S)-2-methylpiperazin-1-yl)ethanone (I-32)

The title compound was prepared from (S)-tert-butyl 4-(2-(4-(adamantan-1-yl)phenoxy)acetyl)-3-methylpiperazine-1-carboxylate (0.18 g, 0.38 mmol), prepared from the example 31, according to the example 30, which was given 2-(4-(adamantan-1-yl)phenoxy)-1-((S)-2-methylpiperazin-1-yl) ethanone as a white solid (0.132 g, 93.6% yield).

$^1$H-NMR (DMSO-d$_6$, 400 MHz) δ 7.32 (2H, d, aromatic-H), 6.91 (2H, d, aromatic-H), 4.88 (2H, s, OCH$_2$CO), 4.30 (2H, m, piperazine), 3.50 (2H, m, piperazine), 3.34 (2H, m, piperazine), 3.25 (1H, m, piperazine), 2.56 (3H, d, CH$_3$), 2.10 (3H, brs, adamantyl-H), 1.89 (6H, m, adamantyl-H), 1.78 (6H, m, adamantyl-H).

Example 33

(R)-tert-Butyl 4-(2-(4-(Adamantan-1-yl)phenoxy) acetyl)-3-methylpiperazine-1-carboxylate (I-33)

The title compound was prepared from 2-(4-(adamantan-1-yl)phenoxy)acetic acid (0.2 g, 0.69 mmol) and (R)-tert-butyl 3-methylpiperazine-1-carboxylate (0.139 g, 0.69 mmol) according to the example 1, which was given (R)-tert-butyl 4-(2-(4-(adamantan-1-yl)phenoxy)acetyl)-3-methylpiperazine-1-carboxylate as a white solid (0.297 g, 91.0% yield).

$^1$H-NMR (DMSO-d$_6$, 400 MHz) δ 7.30 (2H, d, aromatic-H), 6.89 (2H, d, aromatic-H), 4.84 (2H, s, OCH$_2$CO), 4.54 (1H, m, piperazine), 4.12 (2H, m, piperazine), 3.90 (2H, m, piperazine), 2.98 (2H, m, piperazine), 2.48 (3H, d, CH$_3$), 2.14 (3H, brs, adamantyl-H), 1.89 (6H, m, adamantyl-H), 1.78 (6H, m, adamantyl-H), 1.47 (9H, s, (CH$_3$)$_3$).

Example 34

2-(4-(Adamantan-1-yl)phenoxy)-1-((R)-2-methylpiperazin-1-yl)ethanone (I-34)

The title compound was prepared from (R)-tert-butyl 4-(2-(4-(adamantan-1-yl)phenoxy)acetyl)-3-methylpiperazine-1-carboxylate (0.18 g, 0.38 mmol), prepared from the example 33, according to the example 30, which was given 2-(4-(adamantan-1-yl)phenoxy)-1-((R)-2-methylpiperazin-1-yl) ethanone as a white solid (0.129 g, 91.4% yield).

$^1$H-NMR (DMSO-d$_6$, 400 MHz) δ 7.32 (2H, d, aromatic-H), 6.91 (2H, d, aromatic-H), 4.88 (2H, s, OCH$_2$CO), 4.30 (2H, m, piperazine), 3.50 (2H, m, piperazine), 3.34 (2H, m, piperazine), 3.25 (1H, m, piperazine), 2.56 (3H, d, CH$_3$), 2.10 (3H, brs, adamantyl-H), 1.89 (6H, m, adamantyl-H), 1.78 (6H, m, adamantyl-H).

Example 35

2-(4-(Adamantan-1-yl)phenoxy)-1-(4-(2-hydroxyethyl)piperazin-1-yl)ethanone (I-35)

The title compound was prepared from 2-(4-(adamantan-1-yl)phenoxy)acetic acid (0.15 g, 0.52 mmol) and 2-(piperazin-1-yl)ethanol (0.068 g, 0.52 mmol) according to the example 1, which was given 2-(4-(adamantan-1-yl)phenoxy)-1-(4-(2-hydroxyethyl)piperazin-1-yl)ethanone as a white solid (0.187 g, 90.3% yield).

$^1$H-NMR (MeOH-d$_4$, 500 MHz) δ 7.17 (2H, d, aromatic-H), 6.78 (2H, d, aromatic-H), 4.65 (2H, s, OCH$_2$CO), 3.58 (2H, t, CH$_2$), 3.51 (4H, m, piperazine), 2.45 (4H, m, piperazine), 2.41 (2H, t, CH$_2$), 1.96 (3H, brs, adamantyl-H), 1.80 (6H, m, adamantyl-H), 1.69 (6H, m, adamantyl-H).

Example 36

2-(4-(Adamantan-1-yl)phenoxy)-1-(4-(prop-2-yn-1-yl)piperazin-1-yl)ethanone (I-36)

The title compound was prepared from 2-(4-(adamantan-1-yl)phenoxy)acetic acid (0.13 g, 0.45 mmol) and 1-(prop-2-yn-1-yl)piperazine (0.056 g, 0.45 mmol) according to the example 1, which was given 2-(4-(adamantan-2-yl)phenoxy)-1-(4-(prop-2-yn-1-yl)piperazin-1-yl)ethanone as a white solid (0.158 g, 89.3% yield).

$^1$H-NMR (MeOH-d$_4$, 500 MHz) δ 7.17 (2H, d, aromatic-H), 6.78 (2H, d, aromatic-H), 4.66 (2H, s, OCH$_2$CO), 3.52 (4H, m, piperazine), 3.21 (2H, s, CH$_2$), 2.56 (1H, m, CH), 2.45 (4H, m, piperazine), 1.96 (3H, brs, adamantyl-H), 1.80 (6H, m, adamantyl-H), 1.69 (6H, m, adamantyl-H).

Example 37

2-(4-(Adamantan-1-yl)phenoxy)-N-(4-(4-methylpiperazin-1-yl)phenyl)acetamide (I-37)

The title compound was prepared from 2-(4-(adamantan-1-yl)phenoxy)acetic acid (0.2 g, 0.69 mmol) and 4-(4-methylpiperazin-1-yl)aniline (0.133 g, 0.69 mmol) according to the example 1, which was given 2-(4-(adamantan-1-yl)phenoxy)-N-(4-(4-methylpiperazin-1-yl)phenyl)acetamide as a white solid (0.30 g, 93.4% yield).

$^1$H-NMR (DMSO-d$_6$, 400 MHz) δ 9.79 (1H, s, (C═O) NH), 7.45 (2H, d, aromatic-H), 7.25 (2H, d, aromatic-H), 6.88 (4H, m, aromatic-H), 4.58 (2H, s, OCH$_2$CO), 3.04 (4H, m, piperazine), 2.48 (4H, m, piperazine), 2.19 (3H, s, CH₃), 2.01 (3H, brs, adamantyl-H), 1.80 (6H, m, adamantyl-H), 1.69 (6H, m, adamantyl-H).

Example 38

2-(4-(Adamantan-1-yl)phenoxy)-N-(4-(1,1-dioxidothiomorpholino)phenyl)acetamide (I-38)

The title compound was prepared from 2-(4-(adamantan-1-yl)phenoxy)acetic acid (0.2 g, 0.69 mmol) and 4-(4-aminophenyl)thiomorpholine 1,1-dioxide (0.158 g, 0.69 mmol) according to the example 1, which was given 2-(4-(adamantan-1-yl)phenoxy)-N-(4-(1,1-dioxidothiomorpholino)phenyl)acetamide as a white solid (0.31 g, 89.8% yield).
$^1$H-NMR (DMSO-d₆, 400 MHz) δ 9.94 (1H, s, (C=O) NH), 7.58 (2H, d, aromatic-H), 7.34 (2H, d, aromatic-H), 7.05 (2H, d, aromatic-H), 6.98 (2H, d, aromatic-H), 4.67 (2H, s, OCH₂CO), 3.77 (4H, m, thiomorpholine), 3.18 (4H, m, thiomorpholine), 2.04 (3H, brs, adamantyl-H), 1.88 (6H, m, adamantyl-H), 1.74 (6H, m, adamantyl-H).

Example 39

2-(4-(Adamantan-1-yl)phenoxy)-1-(3-(trifluoromethyl)-5,6-dihydro-[1,2,4]triazolo[4,3-a]pyrazin-7(8H)-yl)ethanone (I-39)

The title compound was prepared from 2-(4-(adamantan-1-yl)phenoxy)acetic acid (0.08 g, 0.27 mmol) and 3-(trifluoromethyl)-5,6,7,8-tetrahydro-[1,2,4]triazolo[4,3-a]pyrazine (0.053 g, 0.27 mmol) according to the example 1, which was given 2-(4-(adamantan-1-yl)phenoxy)-1-(3-(trifluoromethyl)-5,6-dihydro-[1,2,4]triazolo[4,3-a]pyrazin-7(8H)-yl) ethanone as a white solid (0.10 g, 78.1% yield).
$^1$H-NMR (CDCl₃, 400 MHz) δ 7.28 (2H, d, aromatic-H), 6.88 (2H, d, aromatic-H), 5.17 (2H, m, pyrazine), 4.78 (2H, s, OCH₂CO), 4.12 (4H, m, pyrazine), 2.08 (3H, brs, adamantyl-H), 1.86 (6H, m, adamantyl-H), 1.74 (6H, m, adamantyl-H).

Example 40 N-(Adamantan-1-yl)-2-(4-adamantan-1-yl)phenoxy)acetamide (I-40)

The title compound was prepared from 2-(4-(adamantan-1-yl)phenoxy)acetic acid (0.2 g, 0.69 mmol) and adamantan-1-amine (0.105 g, 0.69 mmol) according to the example 1, which was given N-(adamantan-1-yl)-2-(4-(adamantan-1-yl)phenoxy)acetamide as a white solid (0.27 g, 92.1% yield).
$^1$H-NMR (DMSO-d₆, 400 MHz) δ 7.24 (2H, d, aromatic-H), 6.81 (2H, d, aromatic-H), 4.32 (2H, s, OCH₂CO), 2.03 (6H, brs, adamantyl-H), 1.93 (3H, m, adamantyl-H), 1.80 (6H, m, adamantyl-H), 1.70 (9H, m, adamantyl-H), 1.60 (6H, m, adamantyl-H).

Example 41

2-(4-(Adamantan-1-yl)phenoxy)-N-(3-hydroxyadamantan-1-yl)acetamide (I-41)

The title compound was prepared from 2-(4-(adamantan-1-yl)phenoxy)acetic acid (0.2 g, 0.69 mmol) and 3-aminoadamantan-1-ol hydrate (0.129 g, 0.69 mmol) according to the example 1, which was given 2-(4-(adamantan-1-yl)phenoxy)-N-(3-hydroxyadamantan-1-yl)acetamide as a white solid (0.275 g, 90.4% yield).
$^1$H-NMR (DMSO-d₆, 400 MHz) δ 7.33 (1H, s, (C=O) NH), 7.23 (2H, d, aromatic-H), 6.82 (2H, d, aromatic-H), 4.49 (1H, s, OH), 4.32 (2H, s, OCH₂CO), 2.11 (2H, brs, adamantyl-H), 2.06 (3H, brs, adamantyl-H), 1.80 (12H, m, adamantyl-H), 1.73 (6H, m, adamantyl-H), 1.50 (5H, m, adamantyl-H).

Example 42

2-(4-(Adamantan-1-yl)-2-chlorophenoxy)-1-(4-methylpiperazin-1-yl)ethanone (I-42)

Step 1: 1-(3-Chloro-4-methoxyphenyl)adamantane

The title compound was prepared from 1-chloro-2-methoxybenzene (10 mL) and 1-bromoadamantane (3.25 g, 15.25 mmol) according to the step 1 of the example 5, which was given 1-(3-chloro-4-methoxyphenyl)adamantane (3.52 g, 84.4% yield).
$^1$H-NMR (CDCl₃, 400 MHz) δ 7.35 (1H, d, aromatic-H), 7.18 (1H, m, aromatic-H), 6.87 (1H, d, aromatic-H), 3.87 (3H, s, OCH₃), 2.08 (3H, br, adamantyl-H), 1.86 (6H, m, adamantyl-H), 1.74 (6H, m, adamantyl-H).

Step 2: 4-(Adamantan-1-yl)-2-chlorophenol

The title compound was prepared from 1-(3-chloro-4-methoxyphenyl)adamantane (3.0 g, 10.83 mmol) according to the step 2 of the example 5, which was given 4-(adamantan-1-yl)-2-chlorophenol (2.70 g, 95.2% yield).
$^1$H-NMR (CDCl₃, 400 MHz) δ 7.27 (1H, d, aromatic-H), 7.16 (1H, m, aromatic-H), 6.95 (1H, d, aromatic-H), 5.35 (1H, bs, OH), 2.08 (3H, s, adamantyl-H), 1.85 (6H, m, adamantyl-H), 1.76 (6H, m, adamantyl-H).

Step 3: Ethyl 2-(4-(adamantan-1-yl)-2-chlorophenoxy)acetate

The title compound was prepared from 4-(adamantan-1-yl)-2-chlorophenol (2.0 g, 7.61 mmol) according to the step 3 of the example 5, which was given ethyl 2-(4-(adamantan-1-yl)-2-chlorophenoxy)acetate (2.52 g, 95.4% yield).
$^1$H-NMR (CDCl₃, 400 MHz) δ 7.35 (1H, d, aromatic-H), 7.15 (1H, m, aromatic-H), 6.80 (1H, d, aromatic-H), 4.68 (2H, s, OCH₂CO), 4.26 (2H, q, OCH₂CH₃), 2.04 (3H, brs, adamantyl-H), 1.85 (6H, m, adamantyl-H), 1.75 (6H, m, adamantyl-H), 1.29 (3H, t, CH₃).

Step 4: 2-(4-(Adamantan-1-yl)-2-chlorophenoxy)acetic acid

The title compound was prepared from ethyl 2-(4-(adamantan-1-yl)-2-chlorophenoxy)acetate (1.1 g, 3.15 mmol), prepared from the step 3, according to the step 4 of the example 5, which was given 2-(4-(adamantan-1-yl)-2-chlorophenoxy)acetic acid (0.92 g, 91.4% yield).
$^1$H-NMR (DMSO-d₆, 400 MHz) δ 7.41 (1H, d, aromatic-H), 7.30 (1H, m, aromatic-H), 6.99 (1H, d, aromatic-H), 4.81 (2H, s, OCH₂CO), 2.10 (3H, brs, adamantyl-H), 1.87 (6H, m, adamantyl-H), 1.78 (6H, m, adamantyl-H).

Step 5: 2-(4-(Adamantan-1-yl)-2-chlorophenoxy)-1-(4-methylpiperazin-1-yl)ethanone (I-42)

The title compound was prepared from 2-(4-(adamantan-1-yl)-2-chlorophenoxy)acetic acid (0.2 g, 0.62 mmol), prepared from the step 4, and 1-methylpiperazine (0.062 g, 0.62 mmol) according to the example 1, which was given 2-(4-

(adamantan-1-yl)-2-chlorophenoxy)-1-(4-methylpiperazin-1-yl)ethanone as a white solid (0.231 g, 92.0% yield).

$^1$H-NMR (DMSO-$d_6$, 400 MHz) δ 7.39 (1H, d, aromatic-H), 7.28 (1H, m, aromatic-H), 6.99 (1H, d, aromatic-H), 4.95 (2H, s, OCH$_2$CO), 3.51 (4H, m, piperazine), 2.35 (4H, m, piperazine), 2.24 (3H, s, CH$_3$), 2.03 (3H, brs, adamantyl-H), 1.81 (6H, m, adamantyl-H), 1.70 (6H, m, adamantyl-H).

Example 43

4-(2-(4-(Adamantan-1-yl)phenoxy)acetyl)-1-methylpiperazin-1-ium methanesulfonate (I-43)

To a solution of 2-(4-(Adamantan-1-yl)phenoxy)-1-(4-methylpiperazin-1-yl)ethanone (1.0 g, 2.7 mmol), prepared from the example 3, in acetone (2 mL) was added methanesulfonic acid (0.18 mL, 2.7 mmol) and stirred at room temperature for 3 h. The reaction mixture was filtered and dried in vacuum to afford a 4-(2-(4-(adamantan-1-yl)phenoxy)acetyl)-1-methylpiperazin-1-ium methanesulfonate as a crystalline white solid (1.1 g, 87% yield).

$^1$H-NMR (MeOH-$d_4$, 400 MHz) δ 7.28 (2H, d, aromatic-H), 6.91 (2H, d, aromatic-H), 4.82 (2H, s, OCH$_2$CO), 4.64 (1H, d, piperazine), 4.24 (1H, d, piperazine), 3.54 (3H, m, piperazine), 3.10 (3H, m, piperazine), 2.94 (3H, s, CH$_3$S), 2.71 (3H, s, CH$_3$), 2.06 (3H, brs, adamantyl-H), 1.89 (6H, m, adamantyl-H), 1.80 (6H, m, adamantyl-H).

Example 44

4-(2-(4-(Adamantan-1-yl)phenoxy)acetyl)-1-methylpiperazin-1-ium 3-carboxy-2-(carboxymethyl)-2-hydroxypropanoate (I-44)

The title compound was prepared from 2-(4-(adamantan-1-yl)phenoxy)-1-(4-methylpiperazin-1-yl)ethanone (1.0 g, 2.7 mmol), prepared from the example 3, and citric acid (0.52 g, 2.7 mmol) according to the example 43, which was given 4-(2-(4-(adamantan-1-yl)phenoxy)acetyl)-1-methylpiperazin-1-ium 3-carboxy-2-(carboxymethyl)-2-hydroxypropanoate as a crystalline white solid (1.43 g, 94% yield).

$^1$H-NMR (MeOH-$d_4$, 400 MHz) δ 7.27 (2H, d, aromatic-H), 6.90 (2H, d, aromatic-H), 4.79 (2H, s, OCH$_2$CO), 3.85 (4H, brs, piperazine), 3.11 (4H, d, piperazine), 2.85 (2H, d, CH$_2$), 2.76 (3H, s, CH$_3$), 2.73 (2H, d, CH$_2$), 2.06 (3H, brs, adamantyl-H), 1.89 (6H, m, adamantyl-H), 1.79 (6H, m, adamantyl-H).

Example 45

4-(2-(4-(Adamantan-1-yl)phenoxy)acetyl)-1-methylpiperazin-1-ium (Z)-3-carboxyacrylate (I-45)

The title compound was prepared from 2-(4-(adamantan-1-yl)phenoxy)-1-(4-methylpiperazin-1-yl)ethanone (1.0 g, 2.7 mmol), prepared from the example 3, and maleic acid (0.31 g, 2.7 mmol) according to the example 43, which was given 4-(2-(4-(adamantan-1-yl)phenoxy)acetyl)-1-methylpiperazin-1-ium (Z)-3-carboxyacrylate as a crystalline white solid (1.01 g, 77% yield).

$^1$H-NMR (DMSO-$d_6$, 400 MHz) δ 7.25 (2H, d, aromatic-H), 6.86 (2H, d, aromatic-H), 6.06 (1H, s, CH=CH), 4.82 (2H, s, OCH$_2$CO), 3.68 (4H, brs, piperazine), 3.15 (4H, d, piperazine), 2.77 (3H, s, CH$_3$), 2.06 (3H, brs, adamantyl-H), 1.82 (6H, m, adamantyl-H), 1.72 (6H, m, adamantyl-H).

Example 46

4-(3-(4-(Adamantan-1-yl)phenoxy)acetyl)-1-methylpiperazin-1-ium 4-methylbenzenesulfonate (I-46)

The title compound was prepared from 2-(4-(adamantan-1-yl)phenoxy)-1-(4-methylpiperazin-1-yl)ethanone (1.0 g, 2.7 mmol), prepared from the example 3, and p-toluenesulfonic acid (0.52 g, 2.7 mmol) according to the example 43, which was given 4-(2-(4-(adamantan-1-yl)phenoxy)acetyl)-1-methylpiperazin-1-ium 4-methylbenzenesulfonate as a crystalline white solid (1.2 g, 82% yield).

$^1$H-NMR (DMSO-$d_6$, 400 MHz) δ 9.69 (1H, brs, COOH), 7.49 (2H, d, aromatic-H), 7.24 (2H, d, aromatic-H), 7.12 (2H, d, aromatic-H), 6.86 (2H, d, aromatic-H), 4.83 (2H, s, OCH$_2$CO), 4.39 (1H, brs, piperazine), 4.05 (1H, brs, piperazine), 3.40 (3H, d, piperazine), 3.05 (3H, d, piperazine), 2.83 (3H, s, CH$_3$), 2.29 (3H, s, PhCH$_3$) 2.04 (3H, brs, adamantyl-H), 1.82 (6H, m, adamantyl-H), 1.72 (6H, m, adamantyl-H).

Example 47

4-(2-(4-(Adamantan-1-yl)phenoxy)acetyl)-1-methylpiperazin-1-ium (2R,3R)-3-carboxy-2,3-dihydroxypropanoate (I-47)

The title compound was prepared from 2-(4-(adamantan-1-yl)phenoxy)-1-(4-methylpiperazin-1-yl)ethanone (1.0 g, 2.7 mmol), prepared from the example 3, and L-(+)-tartaric acid (0.41 g, 2.7 mmol) according to the example 43, which was given 4-(2-(4-(adamantan-1-yl)phenoxy)acetyl)-1-methylpiperazin-1-ium (2R,3R)-3-carboxy-2,3-dihydroxypropanoate as a crystalline white solid (1.2 g, 85% yield).

$^1$H-NMR (DMSO-$d_6$, 400 MHz) δ 7.24 (2H, d, aromatic-H), 6.84 (2H, d, aromatic-H), 4.78 (2H, s, OCH$_2$CO), 4.25 (2H, s, OHCHCHOH), 3.54 (4H, s, piperazine), 2.60 (4H, d, piperazine), 2.38 (3H, s, CH$_3$), 2.04 (3H, brs, adamantyl-H), 1.82 (6H, m, adamantyl-H), 1.72 (6H, m, adamantyl-H).

Example 48

4-(2-(4-(Adamantan-1-yl)phenoxy)acetyl)-1-methylpiperazin-1-ium 3-carboxypropanoate (I-48)

The title compound was prepared from 2-(4-(adamantan-1-yl)phenoxy)-1-(4-methylpiperazin-1-yl)ethanone (1.0 g, 2.7 mmol), prepared from the example 3, and succinic acid (0.41 g, 2.7 mmol) according to the example 43, which was given 4-(2-(4-(adamantan-1-yl)phenoxy)acetyl)-1-methylpiperazin-1-ium 3-carboxypropanoate as a crystalline white solid (0.95 g, 72% yield).

$^1$H-NMR (MeOH-$d_4$, 400 MHz) δ 7.28 (2H, d, aromatic-H), 6.89 (2H, d, aromatic-H), 4.77 (2H, s, OCH$_2$CO), 3.68 (4H, d, piperazine), 2.69 (4H, d, piperazine), 2.54 (4H, s, CH$_2$CH$_2$), 2.45 (3H, s, CH$_3$), 2.06 (3H, brs, adamantyl-H), 1.89 (6H, m, adamantyl-H), 1.80 (6H, m, adamantyl-H).

Example 49

4-(2-(4-(Adamantan-1-yl)phenoxy)acetyl)-1-methylpiperazin-1-ium hydrogensulfate (I-49)

The title compound was prepared from 2-(4-(adamantan-1-yl)phenoxy)-1-(4-methylpiperazin-1-yl)ethanone (1.0 g, 2.7 mmol), prepared from the example 3, and sulfuric acid (0.15 mL, 2.7 mmol) according to the example 43, which was given 4-(2-(4-(adamantan-1-yl)phenoxy)acetyl)-1-methylpiperazin-1-ium hydrogensulfate as a crystalline white solid (1.07 g, 85% yield).

$^1$H-NMR (DMSO-d$_6$, 400 MHz) δ 7.25 (2H, d, aromatic-H), 6.87 (2H, d, aromatic-H), 4.84 (2H, s, OCH$_2$CO), 4.45 (1H, brs, piperazine), 3.95 (1H, brs, piperazine), 3.30 (6H, brs, piperazine), 2.84 (3H, s, CH$_3$), 2.04 (3H, brs, adamantyl-H), 1.82 (6H, m, adamantyl-H), 1.72 (6H, m, adamantyl-H).

Example 50

4-(2-(4-(Adamantan-1-yl)phenoxy)acetyl)-1-methylpiperazin-1-ium dihydrogenphosphate (I-50)

The title compound was prepared from 2-(4-(adamantan-1-yl)phenoxy)-1-(4-methylpiperazin-1-yl)ethanone (1.0 g, 2.7 mmol), prepared from the example 3, and phosphoric acid (0.19 mL, 2.7 mmol) according to the example 43, which was given 4-(2-(4-(adamantan-1-yl)phenoxy)acetyl)-1-methylpiperazin-1-ium dihydrogenphosphate as a crystalline white solid (0.95 g, 75% yield).

$^1$H-NMR (MeOH-d$_4$, 400 MHz) δ 7.28 (2H, d, aromatic-H), 6.90 (2H, d, aromatic-H), 4.80 (2H, s, OCH$_2$CO), 3.92 (4H, brs, piperazine), 3.22 (4H, d, piperazine), 2.83 (3H, s, CH$_3$), 2.06 (3H, brs, adamantyl-H), 1.89 (6H, m, adamantyl-H), 1.79 (6H, m, adamantyl-H).

Example 51

4-(2-(4-(Adamantan-1-yl)phenoxy)acetyl)-1-methylpiperazin-1-ium (E)-3-carboxyacrylate (I-51)

The title compound was prepared from 2-(4-(adamantan-1-yl)phenoxy)-1-(4-methylpiperazin-1-yl)ethanone (1.0 g, 2.7 mmol), prepared from the example 3, and fumaric acid (0.41 g, 2.7 mmol) according to the example 43, which was given 4-(2-(4-(adamantan-1-yl)phenoxy)acetyl)-1-methylpiperazin-1-ium (E)-3-carboxyacrylate as a crystalline white solid (1.14 g, 87% yield).

$^1$H-NMR (DMSO-d$_6$, 400 MHz) δ 7.24 (2H, d, aromatic-H), 6.87 (2H, d, aromatic-H), 6.12 (2H, s, CH=CH), 4.82 (2H, s, OCH$_2$CO), 3.65 (4H, brs, piperazine), 3.18 (4H, d, piperazine), 2.78 (3H, s, CH$_3$), 2.05 (3H, brs, adamantyl-H), 1.82 (6H, m, adamantyl-H), 1.72 (6H, m, adamantyl-H).

Example 52

4-(2-(4-(Adamantan-1-yl)phenoxy)acetyl)-1-methylpiperazin-1-ium 2,2,2-trifluoroacetate (I-52)

The title compound was prepared from 2-(4-(adamantan-1-yl)phenoxy)-1-(4-methylpiperazin-1-yl)ethanone (1.0 g, 2.7 mmol), prepared from the example 3, and trifluoroacetic acid (0.31 g, 2.7 mmol) according to the example 43, which was given 4-(2-(4-(adamantan-1-yl)phenoxy)acetyl)-1-methylpiperazin-1-ium 2,2,2-trifluoroacetate as a crystalline white solid (1.22 g, 93% yield).

$^1$H-NMR (DMSO-d$_6$, 400 MHz) δ 7.25 (2H, d, aromatic-H), 6.86 (2H, d, aromatic-H), 4.83 (2H, s, OCH$_2$CO), 3.67 (4H, brs, piperazine), 3.28 (4H, d, piperazine), 2.88 (3H, s, CH$_3$), 2.06 (3H, brs, adamantyl-H), 1.84 (6H, m, adamantyl-H), 1.74 (6H, m, adamantyl-H).

Experiment 1

Assay for Inhibition of HIF-1α-Mediated Transcriptional Activity (HRE Reporter Assay)

This assay was performed to determine whether the compounds according to the present invention exhibited the anti-cancer activity or not. The compounds can be developed as anti-cancer drugs, because the compounds inhibiting HIF-1α-mediated HRE transcriptional activity induced by hypoxia can suppress the growth and metastasis of cancer.

Inhibitory effects of the compounds according to the present invention, from Formula I-1 to I-42, on HIF-1α-mediated transcriptional activity were evaluated using this assay. pGL3-HRE-luciferase vector was constructed as follows. Six copies of HRE (Hypoxia Responsive Element, 5'-ACGTG-3') from human VEGF genes were inserted into the multi-cloning site of a pGL3-basic vector (Promega). A luciferase gene was used as a reporter gene.

In detail, HCT116 (ATCC #CCL-247) human colon cancer cells were seeded in 48-well cell culture plates. The cells were co-transfected with 25 ng of pGL3-HRE-luciferase and 2.5 ng of Renila control vectors using Polyfect reagent next day. After 24 hours of incubation, the cells were incubated for an additional 4 hours with replaced cell culture media. The cells were treated with various concentrations (0, 1, 3, 5, 10, and 20 μM) of the above compounds according to the present invention and incubated for 12 hours under hypoxia (1% O$_2$, 94% N$_2$, and 5% CO$_2$). The luciferase assay was performed using a dual-luciferase reporter assay system (Promega). After cell lysate preparation with RIPA buffer, induced luciferase activity under hypoxic conditions was determined to examine inhibitory effects of the compounds according to the present invention, from Formula I-1 to I-42, on HIF-1α-mediated transcriptional activity. The results are assigned to four activity ranges and those assignments are reported in Table 1.

Inhibitory activity against HIF-1α (10 μM): A (76~100%), B (51~75%), C (26~50%), D (1~25%)

TABLE 1

Inhibition of HIF-1α-mediated HRE transcriptional activity

| Compound | Inhibitory activity against HIF-1α (10 μM) |
|---|---|
| I-1 | B |
| I-2 | A |
| I-3 | A |
| I-4 | A |
| I-5 | A |
| I-6 | A |
| I-7 | B |
| I-8 | B |
| I-9 | A |
| I-10 | C |
| I-11 | A |
| I-12 | A |
| I-13 | B |
| I-14 | B |
| I-15 | C |
| I-16 | B |
| I-17 | C |
| I-18 | C |
| I-19 | C |
| I-20 | A |
| I-21 | C |
| I-22 | B |
| I-23 | A |
| I-24 | A |
| I-25 | B |
| I-26 | A |
| I-27 | A |
| I-28 | B |
| I-29 | B |
| I-30 | A |
| I-31 | A |
| I-32 | A |
| I-33 | A |
| I-34 | B |

TABLE 1-continued

Inhibition of HIF-1α-mediated HRE transcriptional activity

| Compound | Inhibitory activity against HIF-1α (10 μM) |
|---|---|
| I-35 | C |
| I-36 | B |
| I-37 | D |
| I-38 | B |
| I-39 | C |
| I-40 | D |
| I-41 | A |
| I-42 | B |

As shown in above Table 1, the effects of the compounds according to the present invention on HIF-1α-mediated HRE transcriptional activity were determined under hypoxia. The results indicate that the compounds according to the present invention show inhibitory activity against HRE transcription. In particular, 32 compounds of 42 tested compounds exhibited more than 50% HIF-1α inhibitory activity, and 18 compounds showed HIF-1α inhibitory activity more than 75% among the 32 compounds.

As mentioned above, the compounds according to the present invention can be used as effective components for cancer treatment, because the compounds inhibiting HIF-1α-mediated HRE transcriptional activity can suppress the growth and metastasis of cancer. In addition, these compounds displaying anti-angiogenic activity can be considered as effective components to develop the treatment of diabetic retinopathy and rheumatoid arthritis.

Experiment 2

In Vitro Studies for Inhibition of Hypoxia-Induced HIF-1α Accumulation

Inhibition of HIF-1α accumulation by the compounds according to the present invention was determined in HCT116 human colon cancer cells. In particular, western blot analysis was used to identify the compounds, I-3, I-6, I-8, I-16, I-19, I-22-I-24, and I-27-I-36, which inhibited HIF-1α accumulation under hypoxia.

First, HCT116 human colon cancer cells (ATCC #CCL-247) were plated at the concentration of $2 \times 10^5$ cells/ml. After 24 hours, the cells were incubated under hypoxia (1% $O_2$, 94% $N_2$, and 5% $CO_2$, expressed as 1% $O_2$ in FIG. 1) for 4 hours in order to induce HIF-1α accumulation. Cells were treated with the compounds at various concentrations (0, 3, 10, 20, and 30 μM) for 12 hours under hypoxia. The cells were then harvested, and lysed in RIPA buffer to obtain nuclear extracts. Cells grown at 20% $O_2$ (normoxia) were used as control groups to compare HIF-1α-mediated gene expression under each condition. 30 μg of the nuclear extracts per sample was separated by SDS-PAGE (sodium dodecyl sulfate-polyacrylamide gel electrophoresis), and was then transferred to PVDF (polyvinylidene fluoride membrane) membranes. After membranes were probed with HIF-1α antibodies (R&D System), HIF-1α proteins were detected with HRP-conjugated secondary antibodies (Amersham-Pharmacia). GAPDH (Glyceraldehyde 3-phosphate dehydrogenase) was used as an internal control for loading in western blot analysis. The results were shown in FIG. 1. FIG. 1 shows the potency of the compounds according to the present invention that inhibit HIF-1α accumulation.

As shown in FIG. 1, the compounds according to the present invention, I-3, I-6, I-8, I-16, I-19, I-22-I-24, and I-27-I-36, did not affect GAPDH expression levels, but promoted HIF-1α degradation. In particular, the compounds, I-3, I-8, I-16, I-19, I-22, and I-28-I-30, had significant inhibitory effects on HIF-1α accumulation.

As mentioned above, the compounds according to the present invention can be considered as effective components to develop a new anti-cancer agent, because the compounds inhibit HIF-1α accumulation that forms malignant cancer. Furthermore, these compounds inhibiting angiogenesis can be used as effective components for the treatment of diabetic retinopathy and rheumatoid arthritis.

Experiment 3

CAM Assay

CAM (Chick embryo chorioallantoic membrane) assay was conducted as an in vivo model to determine whether the compounds according to the present invention, I-3, I-6, I-19, and I-22, had anti-angiogenic effects or not. DMSO-treated groups were used as negative controls.

According to the present invention, CAM assay was performed as follows.

Fertilized eggs were incubated periodically rolling at 37° C. with 50% humidity for 2-3 days. When eggs were erected, approximately 3 ml of albumin was extracted from the sharp edge of the eggs using a syringe. The hole of the eggs was sealed with a tape to prevent from dryness and contamination, and the hole of the eggs was put down and incubated for 2 to 3 days. After punching a hole with 1.5 cm diameter in the round part of eggs, opague membrane was removed carefully. The compounds (10-20 μg) according to the present invention were placed and spread on thermanox coverslip equally to dry, and then the hole in the round part of eggs put on the upper part of the fertilized eggs that vessels grew. The eggs were examined under the dissecting microscope and the results were given in FIG. 2, after covering the hole with a coverglass to protect it from contamination for 2 days.

Figure 2:
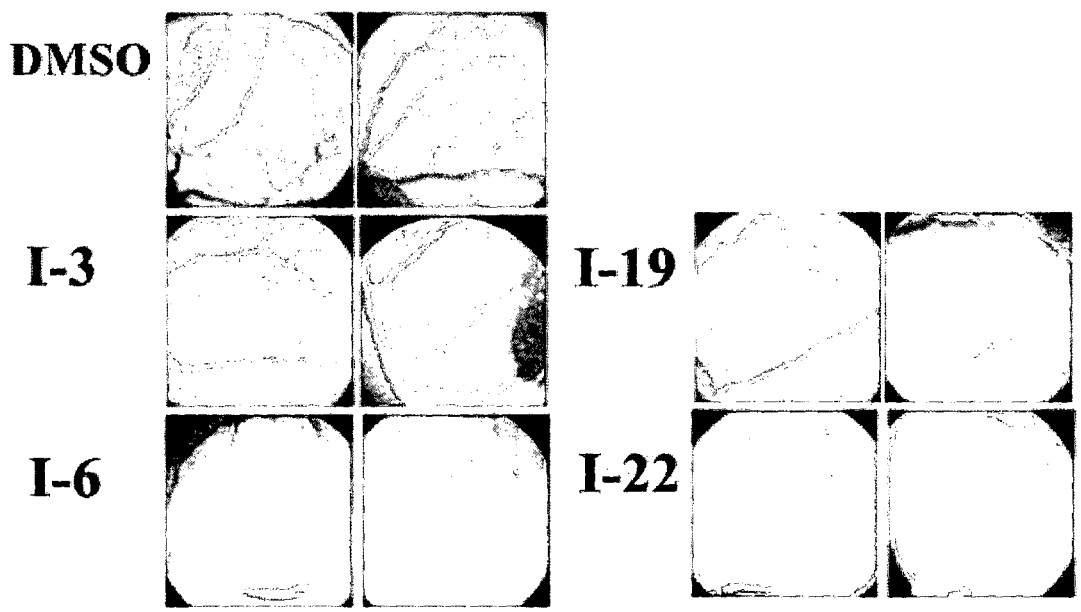
FIG. 2 shows the results of CAM (chick embryo chorioallantoic membrane) assay of the compounds prepared in the present invention.

As shown in FIG. 2, CAM assay was performed to evaluate the compounds prepared in the present invention, I-3, I-6, I-19 and I-22. While many vessels were grown in negative control groups treated with vehicle, DMSO, the compounds according to the present invention inhibited formation of vessels.

As the above results, the compounds according to the present invention showing anti-angiogenic activity can be considered as effective components for developing new treatment of cancer, diabetic retinopathy, and rheumatoid arthritis.

Example 4

In Vivo Anti-Cancer Activity of Compounds by Oral Administration

In vivo anti-cancer activity of the compounds according to the present invention, I-3, I-6, I-8, I-16, I-19, I-22, I-23, and I-24, was measured in mice to evaluate in vivo efficacy by oral administration. Specifically, the nude mice were divided into test groups and control groups, each consisting of 4 mice. In vivo efficacy was evaluated by measuring body weight, tumor volume, and tumor weight.

Female nude mice 6 weeks old (BALB/c nu/nu, Charles River) were bred in germ-free breeding rooms maintained at constant temperature and humidity. After the nude mice were anesthetized, HCT116 colon cancer cells were implanted at a count of 4×10 cells/mouse into the rectum in BALB/c nu/nu mice and then the incisions were closed with surgical clips. The size of tumor was measured by a caliper. When the size of transplanted tumor reached to 50~60 mm³, the above compounds according to the present invention were administered. In more detail, after the above compounds in test groups were dissolved at concentration of 20 mg/kg in a solvent containing 80% of physiological saline, 10% of DMAC (dimethylacetamide), and 10% Tween 80 (hereinafter referred to as 'Solvent A'), 15 kg/ml of dissolved compounds were orally administered once a day. Mice in control groups were treated with 15 kg/ml of Solvent A alone once daily.

Tumor volume and body weight were measured to identify in vivo anti-cancer activity of the compounds according to the present invention by repetitive oral administration. Tumor volume and tumor growth inhibition (TGI) in Table 2 were calculated according to the below Mathematic FIG. 1 and FIG. 2, respectively. Tumor growth inhibition was converted to a percentage in Table 2.

MathFigure 1

$$Tumor\,volume(mm^3) = (Length\,of\,LongAxis,\,mm) \times (Length\,of\,ShortAxis,\,mm)^2 \times 0.5 \quad [\text{Math. 1}]$$

MathFigure 2

$$Tumor\,growth\,inhibition(\%) = \frac{\left(\begin{array}{c}Tumor\,volume(control\,groups) - \\ Tumor\,volume(test\,groups)\end{array}\right)}{Tumor\,volume(control\,groups)} \times 100 \quad [\text{Math. 2}]$$

TABLE 2 in vivo anti-cancer activity of compounds by oral administration

| Group | Dose | Tumor volume (mm³) / TGI (%) | | | | | | | Tumor weight(mg) |
|---|---|---|---|---|---|---|---|---|---|
| (n = 4) | (mg/kg) | day 0 | 3 | 5 | 7 | 10 | 12 | 14 | 14 |
| vehicle Control | 0 | 0.0 ± 0.0 | 34.0 ± 5.6 | 92.3 ± 17.2 | 174.6 ± 38.6 | 260.7 ± 47.6 | 448.6 ± 48.4 | 666.0 ± 76.3 | 2370.6 ± 205.7 |
| I-3 | 20 | 0.0 ± 0.0 | 31.6 ± 5.0 33.2% | 74.8 ± 11.7 35.0% | 133.7 ± 14.8 36.0% | 237.0 ± 24.9 41.6% | 371.4 ± 36.2 44.1% | 587.8 ± 48.4 49.2% | 2074.2 ± 373.8 51.5% |
| I-6 | 20 | 0.0 ± 0.0 | 25.5 ± 7.5 25.0% | 70.1 ± 9.7 24.1% | 128.4 ± 14.0 26.5% | 186.6 ± 15.2 28.4% | 322.5 ± 19.6 28.1% | 476.9 ± 28.1 28.4% | 1703.3 ± 252.2 28.1% |
| I-8 | 20 | 0.0 ± 0.0 | 24.6 ± 5.1 27.6% | 65.5 ± 9.0 29.0% | 122.2 ± 7.9 30.0% | 184.3 ± 10.0 29.3% | 319.7 ± 22.0 28.7% | 471.1 ± 29.0 29.3% | 1634.6 ± 357.2 31.0% |
| I-16 | 20 | 0.0 ± 0.0 | 24.2 ± 6.1 28.6% | 66.7 ± 14.2 27.8% | 125.8 ± 13.6 27.9% | 185.7 ± 20.2 28.8% | 320.4 ± 33.9 28.6% | 471.8 ± 26.0 29.2% | 1655.7 ± 288.4 30.2% |
| I-19 | 20 | 0.0 ± 0.0 | 22.4 ± 5.6 34.1% | 58.8 ± 11.3 36.4% | 110.4 ± 11.2 36.8% | 162.3 ± 10.1 37.7% | 278.8 ± 35.0 37.8% | 404.7 ± 17.6 39.2% | 1392.4 ± 153.0 41.3% |
| I-22 | 20 | 0.0 ± 0.0 | 20.4 ± 1.1 39.8% | 54.7 ± 2.8 40.8% | 98.9 ± 4.8 43.4% | 143.1 ± 6.2 45.1% | 246.4 ± 10.8 45.1% | 347.6 ± 11.8 47.8% | 1197.3 ± 156.3 49.5% |
| I-23 | 20 | 0.0 ± 0.0 | 40.9 ± 8.2 13.5% | 98.0 ± 13.9 14.8% | 182.4 ± 19.9 12.7% | 352.7 ± 53.6 13.1% | 577.3 ± 74.1 13.1% | 987.6 ± 143.7 14.6% | 3659.9 ± 434.8 14.5% |
| I-24 | 20 | 0.0 ± 0.0 | 38.1 ± 6.4 19.5% | 93.8 ± 21.0 18.4% | 176.8 ± 27.6 15.4% | 341.7 ± 58.8 15.8% | 569.1 ± 72.4 14.3% | 990.1 ± 140.3 14.4% | 3685.5 ± 357.5 13.9% |

According to the TGI results in Table 2, the compounds prepared according to the present invention, I-3, I-19, and I-22, displayed significant inhibitory effects on tumor growth.

Moreover, severe side effects and statistically significant changes of body weight in all mice treated compounds were not shown for 14 days, comparing to control groups treated with vehicle. (Table 3)

TABLE 3

Body weight change for 14 days of treatment (%)

| Group | Dose | Days after treatment | | | | | | |
|---|---|---|---|---|---|---|---|---|
| (n = 4) | (mg/kg) | day 0 | 3 | 5 | 7 | 10 | 12 | 14 |
| vehicle Control | 0 | 100.0 ± 0.0 | 101.1 ± 2.1 | 101.1 ± 2.5 | 101.0 ± 3.5 | 100.3 ± 4.8 | 99.3 ± 3.9 | 97.9 ± 2.8 |
| I-3 | 20 | 100.0 ± 0.0 | 103.2 ± 2.8 | 104.7 ± 3.0 | 105.1 ± 2.8 | 104.6 ± 2.7 | 103.1 ± 2.7 | 103.7 ± 4.0 |
| I-6 | 20 | 100.0 ± 0.0 | 103.4 ± 0.6 | 103.6 ± 2.6 | 103.8 ± 3.3 | 105.0 ± 3.1 | 103.8 ± 2.9 | 102.4 ± 3.0 |
| I-8 | 20 | 100.0 ± 0.0 | 102.2 ± 2.8 | 103.4 ± 2.8 | 102.6 ± 2.2 | 102.9 ± 1.5 | 101.9 ± 1.0 | 101.7 ± 2.6 |
| I-16 | 20 | 100.0 ± 0.0 | 104.1 ± 1.6 | 104.2 ± 2.8 | 104.3 ± 1.9 | 105.8 ± 4.2 | 103.2 ± 3.6 | 102.3 ± 3.7 |
| I-19 | 20 | 100.0 ± 0.0 | 104.0 ± 1.6 | 104.7 ± 3.1 | 104.6 ± 4.0 | 105.1 ± 4.3 | 103.4 ± 3.5 | 102.2 ± 3.8 |
| I-22 | 20 | 100.0 ± 0.0 | 104.1 ± 3.5 | 104.1 ± 4.6 | 104.1 ± 3.3 | 105.6 ± 5.1 | 103.8 ± 3.6 | 102.7 ± 4.1 |

TABLE 3-continued

| | | Body weight change for 14 days of treatment (%) | | | | | | |
|---|---|---|---|---|---|---|---|---|
| Group | Dose | Days after treatment | | | | | | |
| (n = 4) | (mg/kg) | day 0 | 3 | 5 | 7 | 10 | 12 | 14 |
| I-23 | 20 | 100.0 ± 0.0 | 100.8 ± 1.1 | 101.0 ± 1.6 | 100.9 ± 0.7 | 101.9 ± 1.1 | 101.6 ± 1.3 | 102.0 ± 2.0 |
| I-24 | 20 | 100.0 ± 0.0 | 103.5 ± 3.0 | 104.0 ± 3.6 | 103.6 ± 3.6 | 105.0 ± 4.0 | 104.9 ± 4.1 | 106.5 ± 4.5 |

From the results of above example 1, 2, 3, and 4, the compounds according to the present invention can be markedly effective for developing anti-cancer pharmaceutical composition, due to excellent HIF-1α inhibitory activity without severe toxicity. Moreover, the compounds can be used for developing new treatment of both diabetic retinopathy and rheumatoid arthritis.

It will be understood that the invention disclosed and defined in this specification extends to all alternative combinations of two or more of the individual features mentioned or evident from the text or drawings. All of these different combinations constitute various alternative aspects of the invention.

INDUSTRIAL APPLICABILITY

The compounds, HIF-1α inhibitors, according to the present invention can be new therapeutic options to develop treatment for various solid cancers such as colon, liver, gastric, and breast cancers. In addition, the compounds can be used as diabetic retinopathy and rheumatoid arthritis aggravated by up-regulation of HIF-1α-mediated VEGFA gene expression under hypoxia.

The invention claimed is:

1. A compound represented by Formula I,

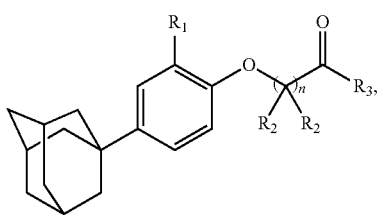

<Formula I> or pharmaceutically acceptable base or acid addition salt, hydrate or solvate thereof, wherein, $R_1$ represents hydrogen, methyl, fluoro or chloro;

$R_2$ represents hydrogen or methyl;

$R_3$ represents,

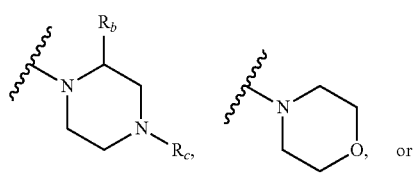

-continued

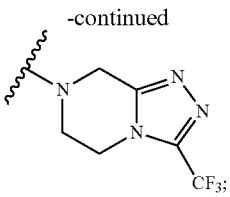

wherein, $R_b$ represents hydrogen, (S)-methyl or (R)-methyl;

$R_c$ represents hydrogen, methyl, isopropyl, tert-butoxycarbonyl(Boc), hydroxyethyl or propynyl; and n represents 1, 2 or 3, provided that when both $R_1$ and $R_2$ represent hydrogen, $R_3$ represents:

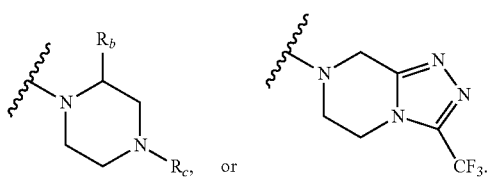

2. The compound according to claim 1, wherein the compound is selected from the group consisting of the following compounds:

2-(4-(Adamantan-1-yl)phenoxy)-1-(4-methylpiperazin-1-yl)ethanone;

2-(4-(Adamantan-1-yl)-2-methylphenoxy)-1-(4-methylpiperazin-1-yl)ethanone;

2-(4-(Adamantan-1-yl)-2-methylphenoxy)-1-morpholinoethanone;

3-(4-(Adamantan-1-yl)phenoxy)-1-(4-methylpiperazin-1-yl)propan-1-one;

3-(4-(Adamantan-1-yl)-2-methylphenoxy)-1-(4-methylpiperazin-1-yl)propan-1-one;

3-(4-(Adamantan-1-yl)-2-methylphenoxy)-1-morpholinopropan-1-one;

4-(4-(Adamantan-1-yl)phenoxy)-1-(4-methylpiperazin-1-yl)butan-1-one;

2-(4-(Adamantan-1-yl)phenoxy)-2-methyl-1-(4-methylpiperazin-1-yl)propan-1-one;

2-(4-(Adamantan-1-yl)-2-fluorophenoxy)-1-(4-methylpiperazin-1-yl)ethanone;

2-(4-(Adamantan-1-yl)phenoxy)-1-(4-isopropylpiperazin-1-yl)ethanone;

tert-Butyl 4-(2-(4-(Adamantan-1-yl)phenoxy)acetyl)piperazine-1-carboxylate;

2-(4-(Adamantan-1-yl)phenoxy)-1-(piperazin-1-yl)ethanone;

(S)-tert-Butyl 4-(2-(4-(adamantan-1-yl)phenoxy)acetyl)-3-methylpiperazine-1-carboxylate;

2-(4-(Adamantan-1-yl)phenoxy)-1-((S)-2-methylpiperazin-1-yl)ethanone;

(R)-tert-Butyl 4-(2-(4-(adamantan-1-yl)phenoxy)acetyl)-3-methylpiperazin-1-carboxylate;

2-(4-(Adamantan-1-yl)phenoxy)-1-((R)-2-methylpiperazin-1-yl)ethanone;

2-(4-(Adamantan-1-yl)phenoxy)-1-(4-(2-hydroxyethyl)piperazin-1-yl)ethanone;

2-(4-(Adamantan-1-yl)phenoxy)-1-(4-(prop-2-yn-1-yl)piperazin-1-yl)ethanone;

2-(4-(Adamantan-1-yl)phenoxy)-1-(3-(trifluoromethyl)-5,6-dihydro-[1,2,4]triazolo[4,3-a]pyrazin-7(8H)-yl)ethanone;

and 2-(4-(Adamantan-1-yl)-2-chlorophenoxy)-1-(4-methylpiperazin-1-yl)ethanone.

3. A compound selected from the group consisting of the following compounds:

4-(2-(4-Adamantan-1-yl)phenoxy)acetyl)-1-methylpiperazin-1-ium chloride;

4-(2-(4-(Adamantan-1-yl)phenoxy)acetyl)-1,1-dimethylpiperazine-1-ium iodide;

4-(2-(4-(Adamantan-1-yl)-2-methylphenoxy)acetyl)-1,1-dimethylpiperazin-1-ium iodide;

4-(3-(4-(Adamantan-1-yl)phenoxy)propanoyl)-1,1-dimethylpiperazin-1-ium iodide;

4-(3-(4-(Adamantan-1-yl)-2-methylphenoxy)propanoyl)-1,1-dimethylpiperazin-1-ium iodide;

4-(4-(4-(Adamantan-1-yl)phenoxy)butanoyl)-1,1-dimethylpiperazin-1-ium iodide;

4-(2-(4-(Adamantan-1-yl)phenoxy)acetyl)-1-methylpiperazin-1-ium methanesulfonate;

4-(2-(4-(Adamantan-1-yl)phenoxy)acetyl)-1-methylpiperazin-1-ium 3-carboxy-2-(carboxymethyl)-2-hydroxypropanoate;

4-(2-(4-(Adamantan-1-yl)phenoxy)acetyl)-1-methylpiperazin-1-ium (Z)-3-carboxyacrylate;

4-(2-(4-(Adamantan-1-yl)phenoxy)acetyl)-1-methylpiperazin-1-ium 4-methylbenzenesulfonate;

4-(2-(4-(Adamantan-1-yl)phenoxy)acetyl)-1-methylpiperazin-1-ium (2R,3R)-3-carboxy-2,3-dihydroxypropanoate;

4-(2-(4-(Adamantan-1-yl)phenoxy)acetyl)-1-methylpiperazin-1-ium 3-carboxypropanoate;

4-(2-(4-(Adamantan-1-yl)phenoxy)acetyl)-1-methylpiperazin-1-ium hydrogensulfate;

4-(2-(4-(Adamantan-1-yl)phenoxy)acetyl)-1-methylpiperazin-1-ium dihydrogenphosphate;

4-(2-(4-(Adamantan-1-yl)phenoxy)acetyl)-1-methylpiperazin-1-ium (E)-3-carboxyacrylate; and 4-(2-(4-(Adamantan-1-yl)phenoxy)acetyl)-1-methylpiperazin-1-ium trifluoroacetate.

* * * * *